United States Patent [19]

Leder et al.

[11] Patent Number: 5,674,734
[45] Date of Patent: Oct. 7, 1997

[54] CELL DEATH PROTEIN

[75] Inventors: Philip Leder, Chestnut Hill; Brian Seed, Boston; Ben Z. Stanger, Brookline, all of Mass.; Tae-Ho Lee, Daejeon, Rep. of Korea; Emily Kim, Chestnut Hill, Mass.

[73] Assignees: President and Fellows of Harvard College, Cambridge; The General Hospital Corporation, Boston, both of Mass.

[21] Appl. No.: 444,005

[22] Filed: May 18, 1995

[51] Int. Cl.$^6$ .............................. C12N 1/20; C07H 21/02; C07H 21/04; C12P 21/06
[52] U.S. Cl. ................... 435/252.3; 536/23.1; 536/23.5; 536/23.4; 435/69.1; 435/69.9; 435/183; 530/350
[58] Field of Search ................................. 536/23.5, 23.1, 536/23.4; 435/69.1, 71.2, 183, 252.3, 69.9; 530/350

[56] References Cited

U.S. PATENT DOCUMENTS 5,500,432  3/1996  Nicolaou et al. ........................ 514/281

FOREIGN PATENT DOCUMENTS

US96/05386  6/1996  WIPO.

OTHER PUBLICATIONS

Hubbard et al., Nature, vol. 372, issued 22/29 Dec. 1994.
Boldin et al., The Journal of Biological Chemistry, vol. 270, No. 1, issued Jan. 6, 1995.
Stanger et al., Cell, vol. 81, issued May 19, 1995.
Alderson et al., "Fas Transduces Activation Signals in Normal Human T Lymphocytes," *J. Exp. Med.* 178:2231–2235 (1993).
Clement et al., "Fas and Tumor Necrosis Factor Receptor–mediated Cell Death: Similarities and Distinctions," *J. Exp. Med.* 180:557–567 (1994).
Crispe, "Fatal Interactions: Fas–Induced Apoptosis of Mature T Cells," *Immunity* 1:347–349 (1994).
Dhein et al., "Induction of Apoptosis By Monoclonal Antibody Anti-Apo-1 Class Switch Variants is Dependent on Cross-Linking of Apo-1 Cell Surface Antigens," *J. Immunol.* 149:3166–3173 (1992).
Heller et al., "Cytotoxicity by Tumor Necrosis Factor is Mediated by Both p55 and p70 Receptors," *Cell* 73:216–217 (1993).
Heller et al., "The p70 Tumor Necrosis Factor Receptor Mediates Cytotoxicity," *Cell* 70:47–56 (1992).
Henkart, "Lymphocyte–Mediated Cytotoxicity: Two Pathways and Multiple Effector Molecules," *Immunity* 1:343–346 (1994).
Itoh et al., "The Polypeptide Encoded by the cDNA for Human Cell Surface Antigen Fas Can Mediate Apoptosis," *Cell* 66:233–243 (1991).
Itoh et al., "A Novel Protein Domain Required for Apoptosis," *J. Biol. Chem.* 268:10932–10937 (1993).

Kagi et al., "Fas and Perforin Pathways as Major Mechanisms of T Cell–Mediated Cytotoxity," *Science* 265:528–530 (1994).
Klas et al., "Activation interferes with the APO-1 pathway in mature human T cells," *International Immunology* 5:625–630 (1993).
Kojima et al., "Two Distinct Pathways of Specific Killing Revealed by Perforin Mutant Cytotoxic T Lymphocytes," *Immunity* 1:357–364 (1994).
Lowin et al., "Cytolytic T–Cell cytotoxicity is mediated through perforin and Fas lytic pathways," *Nature* 370:650–652 (1994).
Oehm et al., "Purification and Molecular Cloning of the APO-1 Cell Surface Antigen, a Member of the Tumor Necrosis Factor/Nerve Growth Factor Receptor Superfamily," *J. Biol. Chem.* 267:10709–10715 (1992).
Singer et al., "The Fas Antigen is Involved is Involved in Peripheral but not Thymic Deletion of T Lymphocytes in T Cell Receptor Transgenic Mice," *Immunity* 1:365–371 (1994).
Smith et al., "The TNF Receptor Superfamily of Cellular and Viral Proteins: Activation, Costimulation, and Death," *Cell* 76:959–962 (1994).
Steller "Mechanisms and Genes of Cellular Suicide," *Science* 267:1445–1462 (1995).
Tartaglia et al., "The two different receptors for tumor necrosis factor mediate distinct cellular responses," *Proc. Natl. Acad. Sci.* 88:9292–9296 (1991).
Tartaglia et al., "A Novel Domain within the 55 kd TNF Receptor Signals Cell Death," *Cell* 74:845–853 (1993).
Tartaglia et al., "Tumor Necrosis Factor's Cytotoxic Activity is Signaled by the p55 TNF Receptor," *Cell* 73:213–216 (1993).
Thompson, "Apoptosis in the Pathogenesis and Treatment of Disease," *Science* 267:1456–1461 (1995).
Trauth et al., "Monoclonal Antibody–Mediated Tumor Regression by Induction of Apoptosis," *Science* 245:301–304 (1989).
Watanabe–Fukanaga et al., "The cDNA Structure, Expression, and Chromosomal Assignment of the Mouse Fas Antigen," *J. Immunol.* 148:1274–1279 (1992).
Watanabe–Fukanaga et al., "Lymphoproliferation disorder in mice explained by defects in Fas antigen that mediates apoptosis," *Nature* 356:314–317 (1992).
Yonehara et al., "A Cell–Killing Monoclonal Antibody (Anti–Fas) To a Cell Surface Antigen Co–Downregulated With the Receptor of Tumor Necrosis Factor," *J. Exp. Med.* 169:1747–1756 (1989).

Primary Examiner—Robert A. Wax
Assistant Examiner—Tekchand Saidha
Attorney, Agent, or Firm—Clark & Elbing LLP

[57] ABSTRACT

Disclosed is a protein, designated RIP, which contains a death domain at its carboxy terminus and a kinase domain at its amino terminus. RIP interacts with the Fas/APO-1 intracellular domain and the TNFR1 intracellular domain. When expressed in transformed host cells, recombinant RIP promotes apoptosis. Also disclosed are DNA molecules encoding RIP, anti-RIP antibodies, and screening methods for discovering inhibitors of RIP-dependent apoptosis.

9 Claims, 3 Drawing Sheets (SEQ ID NO:15)

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CGCGGGACGC GTAAGGAAGT ACAGAAAACA TGC        33

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CGCGGGGCGG CCGCTCTAGA CCAAGCTTTG GATTTC        36

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CGCGGGCGC GCTACCAACG GTGGAAGTCC AAG        33

( 2 ) INFORMATION FOR SEQ ID NO:4:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CGCGGGGCGG CCGCTGCCCG CAGGGCGCA GCCTCA        36

( 2 ) INFORMATION FOR SEQ ID NO:5:

( i ) SEQUENCE CHARACTERISTICS:
        ( A ) LENGTH: 33 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:5:

CGCGGGACGC GTAAGAAGCC CTTGTGCCTG CAG                33

(2) INFORMATION FOR SEQ ID NO:6:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:6:

CGCGGGGCGG CCGCTTTAAC TGGGCTTCAT CCCAGC             36

(2) INFORMATION FOR SEQ ID NO:7:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:7:

CGAAAGAATG GTAACAATGA AGCC                          24

(2) INFORMATION FOR SEQ ID NO:8:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:8:

GGCTTCATTG TTACCATTCT TTCG                          24

(2) INFORMATION FOR SEQ ID NO:9:

(i) SEQUENCE CHARACTERISTICS:
      (A) LENGTH: 62 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:9:

ATTCGTGCCA GCCAGAGCGG CATGGAGCAG AAGCTCATCT CAGAAGAAGA CCTCGCGTAA    60

GC                                                                  62

(2) INFORMATION FOR SEQ ID NO:10:

(i) SEQUENCE CHARACTERISTICS:
      (A) LENGTH: 63 base pairs
      (B) TYPE: nucleic acid
      (C) STRANDEDNESS: single
      (D) TOPOLOGY: linear ( i i ) MOLECULE TYPE: DNA (genomic)

( x i ) SEQUENCE DESCRIPTION: SEQ ID NO:10:

| | | | | | |
|---|---|---|---|---|---|
| GGCCGCTTAC | GCGAGGTCTT | CTTCTGAGAT | GAGCTTCTGC | TCCATGCCGC | TCTGGCTGGC | 60 |
| ACG | | | | | | 63 |

( 2 ) INFORMATION FOR SEQ ID NO:11:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

| | | |
|---|---|---|
| CCCAAGCTTG | TTGGAGATTC | TGAGCAATC | 29 |

( 2 ) INFORMATION FOR SEQ ID NO:12:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

| | | | |
|---|---|---|---|
| CCCGATCTGC | AGGTCATGTA | AGTAGCACAT | GCC | 33 |

( 2 ) INFORMATION FOR SEQ ID NO:13:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

| | | | | | |
|---|---|---|---|---|---|
| CCCCTCGAGT | TAGAGGTCTT | CTTCTGAGAT | GAGCTTTTGC | TCTTTCTTTA | AACTTGCCAC | 60 |

( 2 ) INFORMATION FOR SEQ ID NO:14:

( i ) SEQUENCE CHARACTERISTICS:
        ( A ) LENGTH: 2268 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

| | | | | | |
|---|---|---|---|---|---|
| CATACTGAGC | AAGAACCAAA | AGTGGTGTGT | TGGAGATTCT | GAGCAATCAA | AATGCAACCA | 60 |
| GACATGTCCT | TGGACAATAT | TAAGATGGCA | TCCAGTGACC | TGCTGGAGAA | GACAGACCTA | 120 |
| GACAGCGGAG | GCTTCGGGAA | GGTGTCCTTG | TGTTACCACA | GAAGCCATGG | ATTTGTCATC | 180 |
| CTGAAAAAAG | TATACACAGG | GCCCAACCGC | GCTGAGTACA | ATGAGGTTCT | CTTGGAAGAG | 240 |
| GGGAAGATGA | TGCACAGACT | GAGACACAGT | CGAGTGGTGA | AGCTACTGGG | CATCATCATA | 300 |
| GAAGAAGGGA | ACTATTCGCT | GGTGATGGAG | TACATGGAGA | AGGGCAACCT | GATGCACGTG | 360 |
| CTAAAGACCC | AGATAGATGT | CCCACTTTCA | TTGAAAGGAA | GGATAATCGT | GGAGGCCATA | 420 |

| | | | | | |
|---|---|---|---|---|---|
| GAAGGCATGT | GCTACTTACA | TGACAAAGGT | GTGATACACA | AGGACCTGAA | GCCTGAGAAT | 480 |
| ATCCTCGTTG | ATCGTGACTT | TCACATTAAG | ATAGCCGATC | TTGGTGTGGC | TTCCTTTAAG | 540 |
| ACATGGAGCA | AACTGACTAA | GGAGAAAGAC | AACAAGCAGA | AAGAAGTGAG | CAGCACCACT | 600 |
| AAGAAGAACA | ATGGTGGTAC | CCTTTACTAC | ATGGCACCCG | AACACCTGAA | TGACATCAAT | 660 |
| GCAAAGCCCA | CGGAGAAGTC | GGACGTGTAC | AGCTTTGGCA | TTGTCCTTTG | GCAATATTT | 720 |
| GCAAAAAAGG | AGCCCTATGA | GAATGTCATC | TGTACTGAGC | AGTTCGTGAT | CTGCATAAAA | 780 |
| TCTGGGAACA | GGCCAAATGT | AGAGGAAATC | CTTGAGTACT | GTCCAAGGGA | GATCATCAGC | 840 |
| CTCATGGAGC | GGTGCTGGCA | GGCGATCCCA | GAAGACAGGC | CAACATTTCT | GGCATTGAA | 900 |
| GAAGAATTTA | GGCCTTTTTA | CTTAAGTCAT | TTTGAAGAAT | ATGTAGAAGA | GGATGTGGCA | 960 |
| AGTTTAAAGA | AAGAGTATCC | AGATCAAAGC | CCAGTGCTGC | AGAGAATGTT | TTCACTGCAG | 1020 |
| CATGACTGTG | TACCCTTACC | TCCGAGCAGG | TCAAATTCAG | AACAACCTGG | ATCGCTGCAC | 1080 |
| AGTTCCCAGG | GGCTCCAGAT | GGGTCCTGTG | GAGGAGTCCT | GGTTTTCTTC | CTCCCCAGAG | 1140 |
| TACCCACAGG | ACGAGAATGA | TCGCAGTGTG | CAGGCTAAGC | TGCAAGAGGA | AGCCAGCTAT | 1200 |
| CATGCTTTTG | GAATATTTGC | AGAGAAACAG | ACAAAACCGC | AGCCAAGGCA | GAATGAGGCT | 1260 |
| TACAACAGAG | AGGAGGAAAG | GAAACGAAGG | GTCTCTCATG | ACCCCTTTGC | ACAGCAGAGA | 1320 |
| GCTCGTGAGA | ATATTAAGAG | TGCAGGAGCA | AGAGGTCATT | CTGATCCCAG | CACAACGAGT | 1380 |
| CGTGGAATTG | CAGTGCAACA | GCTGTCATGG | CCAGCCACCC | AAACAGTTTG | GAACAATGGA | 1440 |
| TTGTATAATC | AGCATGGATT | TGGAACTACA | GGTACAGGAG | TTTGGTATCC | GCCAAATCTA | 1500 |
| AGCCAAATGT | ATAGTACTTA | TAAAACTCCA | GTGCCAGAGA | CCAACATACC | GGGAAGCACA | 1560 |
| CCCACCATGC | CATACTTCTC | TGGGCCAGTA | GCAGATGACC | TCATAAAATA | TACTATATTC | 1620 |
| AATAGTTCTG | GTATTCAGAT | TGGAAACCAC | AATTATATGG | ATGTTGGACT | GAATTCACAA | 1680 |
| CCACCAAACA | ATACTTGCAA | AGAAGAGTCG | ACTTCCAGAC | ACCAAGCCAT | CTTTGATAAC | 1740 |
| ACCACTAGTC | TGACTGATGA | ACACCTGAAC | CCTATCAGGG | AAAACCTGGG | AAGGCAGTGG | 1800 |
| AAAAACTGTG | CCCGCAAGCT | GGGCTTCACT | GAGTCTCAGA | TCGATGAAAT | CGACCATGAC | 1860 |
| TATGAAAGAG | ATGGACTGAA | AGAGAAAGTT | TACCAAATGC | TTCAGAAGTG | GCTGATGCGG | 1920 |
| GAAGGCACCA | AAGGGCCAC | AGTGGGAAAG | TTGGCCCAGG | CACTTCACCA | ATGTTGCAGG | 1980 |
| ATAGACCTGC | TGAACCACTT | GATTCGTGCC | AGCCAGAGCT | AAGCCTGGGC | AGGCTCTGGC | 2040 |
| AGTGGGAAGC | AAACTATTTG | TCTGGTGCAC | AAACCCCGTT | TGCCCACTAG | CCTTCAGAAC | 2100 |
| TCTATCTCAG | CATGAGCTCT | GCATTTGAGC | ACACAGGGTC | ATGCAGTTTG | GAACTGGTGG | 2160 |
| ATGGGAAGAG | AAATCTGAAG | CCCACAGTGA | TTCTTCAGAA | CATCCAAGCA | TAAAGACCGC | 2220 |
| TGAATGAATG | GTCGGTCCAT | GACCAGTAGG | AGAAAAAAAA | AAAAAAAG | | 2268 |

( 2 ) INFORMATION FOR SEQ ID NO:15:

( i ) SEQUENCE CHARACTERISTICS:
        ( A ) LENGTH: 656 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:15:

```
Met Gln Pro Asp Met Ser Leu Asp Asn Ile Lys Met Ala Ser Ser Asp
 1               5                  10                  15

Leu Leu Glu Lys Thr Asp Leu Asp Ser Gly Gly Phe Gly Lys Val Ser
             20                  25                  30
```

-continued

| Leu | Cys | Tyr | His | Arg | Ser | His | Gly | Phe | Val | Ile | Leu | Lys | Lys | Val | Tyr |
|  |  | 35 |  |  |  |  | 40 |  |  |  |  | 45 |  |  |  |

| Thr | Gly | Pro | Asn | Arg | Ala | Glu | Tyr | Asn | Glu | Val | Leu | Glu | Glu | Gly |
|  | 50 |  |  |  |  | 55 |  |  |  |  | 60 |  |  |  |

| Lys | Met | Met | His | Arg | Leu | Arg | His | Ser | Arg | Val | Val | Lys | Leu | Leu | Gly |
| 65 |  |  |  |  | 70 |  |  |  |  | 75 |  |  |  |  | 80 |

| Ile | Ile | Ile | Glu | Glu | Gly | Asn | Tyr | Ser | Leu | Val | Met | Glu | Tyr | Met | Glu |
|  |  |  |  | 85 |  |  |  |  | 90 |  |  |  |  | 95 |  |

| Lys | Gly | Asn | Leu | Met | His | Val | Leu | Lys | Thr | Gln | Ile | Asp | Val | Pro | Leu |
|  |  |  | 100 |  |  |  | 105 |  |  |  |  | 110 |  |  |  |

| Ser | Leu | Lys | Gly | Arg | Ile | Ile | Val | Glu | Ala | Ile | Glu | Gly | Met | Cys | Tyr |
|  |  | 115 |  |  |  |  | 120 |  |  |  |  | 125 |  |  |  |

| Leu | His | Asp | Lys | Gly | Val | Ile | His | Lys | Asp | Leu | Lys | Pro | Glu | Asn | Ile |
|  | 130 |  |  |  |  | 135 |  |  |  |  | 140 |  |  |  |  |

| Leu | Val | Asp | Arg | Asp | Phe | His | Ile | Lys | Ile | Ala | Asp | Leu | Gly | Val | Ala |
| 145 |  |  |  |  | 150 |  |  |  |  | 155 |  |  |  |  | 160 |

| Ser | Phe | Lys | Thr | Trp | Ser | Lys | Leu | Thr | Lys | Glu | Lys | Asp | Asn | Lys | Gln |
|  |  |  |  | 165 |  |  |  |  | 170 |  |  |  |  | 175 |  |

| Lys | Glu | Val | Ser | Ser | Thr | Thr | Lys | Lys | Asn | Asn | Gly | Gly | Thr | Leu | Tyr |
|  |  |  | 180 |  |  |  |  | 185 |  |  |  |  | 190 |  |  |

| Tyr | Met | Ala | Pro | Glu | His | Leu | Asn | Asp | Ile | Asn | Ala | Lys | Pro | Thr | Glu |
|  |  | 195 |  |  |  |  | 200 |  |  |  |  | 205 |  |  |  |

| Lys | Ser | Asp | Val | Tyr | Ser | Phe | Gly | Ile | Val | Leu | Trp | Ala | Ile | Phe | Ala |
|  | 210 |  |  |  |  | 215 |  |  |  |  | 220 |  |  |  |  |

| Lys | Lys | Glu | Pro | Tyr | Glu | Asn | Val | Ile | Cys | Thr | Glu | Gln | Phe | Val | Ile |
| 225 |  |  |  |  | 230 |  |  |  |  | 235 |  |  |  |  | 240 |

| Cys | Ile | Lys | Ser | Gly | Asn | Arg | Pro | Asn | Val | Glu | Glu | Ile | Leu | Glu | Tyr |
|  |  |  |  | 245 |  |  |  |  | 250 |  |  |  |  | 255 |  |

| Cys | Pro | Arg | Glu | Ile | Ile | Ser | Leu | Met | Glu | Arg | Cys | Trp | Gln | Ala | Ile |
|  |  |  | 260 |  |  |  |  | 265 |  |  |  |  | 270 |  |  |

| Pro | Glu | Asp | Arg | Pro | Thr | Phe | Leu | Gly | Ile | Glu | Glu | Glu | Phe | Arg | Pro |
|  |  | 275 |  |  |  |  | 280 |  |  |  |  | 285 |  |  |  |

| Phe | Tyr | Leu | Ser | His | Phe | Glu | Glu | Tyr | Val | Glu | Glu | Asp | Val | Ala | Ser |
|  | 290 |  |  |  |  | 295 |  |  |  |  | 300 |  |  |  |  |

| Leu | Lys | Lys | Glu | Tyr | Pro | Asp | Gln | Ser | Pro | Val | Leu | Gln | Arg | Met | Phe |
| 305 |  |  |  |  | 310 |  |  |  |  | 315 |  |  |  |  | 320 |

| Ser | Leu | Gln | His | Asp | Cys | Val | Pro | Leu | Pro | Pro | Ser | Arg | Ser | Asn | Ser |
|  |  |  |  | 325 |  |  |  |  | 330 |  |  |  |  | 335 |  |

| Glu | Gln | Pro | Gly | Ser | Leu | His | Ser | Ser | Gln | Gly | Leu | Gln | Met | Gly | Pro |
|  |  |  | 340 |  |  |  |  | 345 |  |  |  |  | 350 |  |  |

| Val | Glu | Glu | Ser | Trp | Phe | Ser | Ser | Ser | Pro | Glu | Tyr | Pro | Gln | Asp | Glu |
|  |  | 355 |  |  |  |  | 360 |  |  |  |  | 365 |  |  |  |

| Asn | Asp | Arg | Ser | Val | Gln | Ala | Lys | Leu | Gln | Glu | Glu | Ala | Ser | Tyr | His |
|  | 370 |  |  |  |  | 375 |  |  |  |  | 380 |  |  |  |  |

| Ala | Phe | Gly | Ile | Phe | Ala | Glu | Lys | Gln | Thr | Lys | Pro | Gln | Pro | Arg | Gln |
| 385 |  |  |  |  | 390 |  |  |  |  | 395 |  |  |  |  | 400 |

| Asn | Glu | Ala | Tyr | Asn | Arg | Glu | Glu | Glu | Arg | Lys | Arg | Arg | Val | Ser | His |
|  |  |  |  | 405 |  |  |  |  | 410 |  |  |  |  | 415 |  |

| Asp | Pro | Phe | Ala | Gln | Gln | Arg | Ala | Arg | Glu | Asn | Ile | Lys | Ser | Ala | Gly |
|  |  |  | 420 |  |  |  |  | 425 |  |  |  |  | 430 |  |  |

| Ala | Arg | Gly | His | Ser | Asp | Pro | Ser | Thr | Thr | Ser | Arg | Gly | Ile | Ala | Val |
|  |  | 435 |  |  |  |  | 440 |  |  |  |  | 445 |  |  |  |

| Gln | Gln | Leu | Ser | Trp | Pro | Ala | Thr | Gln | Thr | Val | Trp | Asn | Asn | Gly | Leu |

-continued

|  |  |  |  |  | 450 |  |  |  |  | 455 |  |  |  |  | 460 |  |  |  |  |
|---|---|---|---|---|---|---|---|---|---|---|---|---|---|---|---|---|---|---|---|
| Tyr<br>465 | Asn | Gln | His | Gly | Phe<br>470 | Gly | Thr | Thr | Gly | Thr<br>475 | Gly | Val | Trp | Tyr | Pro<br>480 |
| Pro | Asn | Leu | Ser | Gln<br>485 | Met | Tyr | Ser | Thr | Tyr<br>490 | Lys | Thr | Pro | Val | Pro<br>495 | Glu |
| Thr | Asn | Ile | Pro<br>500 | Gly | Ser | Thr | Pro | Thr<br>505 | Met | Pro | Tyr | Phe | Ser<br>510 | Gly | Pro |
| Val | Ala | Asp<br>515 | Asp | Leu | Ile | Lys | Tyr<br>520 | Thr | Ile | Phe | Asn | Ser<br>525 | Ser | Gly | Ile |
| Gln | Ile<br>530 | Gly | Asn | His | Asn | Tyr<br>535 | Met | Asp | Val | Gly | Leu<br>540 | Asn | Ser | Gln | Pro |
| Pro<br>545 | Asn | Asn | Thr | Cys | Lys<br>550 | Glu | Glu | Ser | Thr | Ser<br>555 | Arg | His | Gln | Ala | Ile<br>560 |
| Phe | Asp | Asn | Thr | Thr<br>565 | Ser | Leu | Thr | Asp | Glu<br>570 | His | Leu | Asn | Pro | Ile<br>575 | Arg |
| Glu | Asn | Leu | Gly<br>580 | Arg | Gln | Trp | Lys | Asn<br>585 | Cys | Ala | Arg | Lys | Leu<br>590 | Gly | Phe |
| Thr | Glu | Ser<br>595 | Gln | Ile | Asp | Glu | Ile<br>600 | Asp | His | Asp | Tyr | Glu<br>605 | Arg | Asp | Gly |
| Leu | Lys<br>610 | Glu | Lys | Val | Tyr | Gln<br>615 | Met | Leu | Gln | Lys | Trp<br>620 | Leu | Met | Arg | Glu |
| Gly<br>625 | Thr | Lys | Gly | Ala | Thr<br>630 | Val | Gly | Lys | Leu | Ala<br>635 | Gln | Ala | Leu | His | Gln<br>640 |
| Cys | Cys | Arg | Ile | Asp<br>645 | Leu | Leu | Asn | His | Leu<br>650 | Ile | Arg | Ala | Ser | Gln<br>655 | Ser |

( 2 ) INFORMATION FOR SEQ ID NO:16:

( i ) SEQUENCE CHARACTERISTICS:
        ( A ) LENGTH: 2137 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

| ATGCAACCAG | ACATGTCCTT | GAATGTCATT | AAGATGAAAT | CCAGTGACTT | CCTGGAGAGT | 60 |
| GCAGAACTGG | ACAGCGGAGG | CTTCGGGAAG | GTGTCTCTGT | GTTTCCACAG | AACCCAGGGA | 120 |
| CTCATGATCA | TGAAAACAGT | GTACAAGGGG | CCCAACTGCA | TTGAGCACAA | CGAGGCCCTC | 180 |
| TTGGAGGAGG | CGAAGATGAT | GAACAGACTG | AGACACAGCC | GGGTGGTGAA | GCTCCTGGGC | 240 |
| GTCATCATAG | AGGAAGGGAA | GTACTCCCTG | GTGATGGAGT | ACATGGAGAA | GGGCAACCTG | 300 |
| ATGCACGTGC | TGAAAGCCGA | GATGAGTACT | CCGCTTTCTG | TAAAAGGAAG | GATAATTTTG | 360 |
| GAAATCATTG | AAGGAATGTG | CTACTTACAT | GGAAAAGGCG | TGATACACAA | GGACCTGAAG | 420 |
| CCTGAAAATA | TCCTTGTTGA | TAATGACTTC | CACATTAAGA | TCGCAGACCT | CGGCCTTGCC | 480 |
| TCCTTTAAGA | TGTGGAGCAA | ACTGAATAAT | GAAGAGCACA | ATGAGCTGAG | GGAAGTGGAC | 540 |
| GGCACCGCTA | AGAAGAATGG | CGGCACCCTC | TACTACATGG | CGCCCGAGCA | CCTGAATGAC | 600 |
| GTCAACGCAA | AGCCCACAGA | GAAGTCGGAT | GTGTACAGCT | TGCTGTAGT | ACTCTGGGCG | 660 |
| ATATTTGCAA | ATAAGGAGCC | ATATGAAAAT | GCTATCTGTG | AGCAGCAGTT | GATAATGTGC | 720 |
| ATAAAATCTG | GAACAGGCC | AGATGTGGAT | GACATCACTG | AGTACTGCCC | AAGAGAAATT | 780 |
| ATCAGTCTCA | TGAAGCTCTG | CTGGGAAGCG | AATCCGGAAG | CTCGGCCGAC | ATTTCCTGGC | 840 |
| ATTGAAGAAA | AATTTAGGCC | TTTTTATTTA | AGTCAATTAG | AAGAAAGTGT | AGAAGAGGAC | 900 |

-continued

```
GTGAAGAGTT TAAAGAAAGA GTATTCAAAC GAAAATGCAG TTGTGAAGAG AATGCAGTCT    960
CTTCAACTTG ATTGTGTGGC AGTACCTTCA AGCCGGTCAA ATTCAGCCAC AGAACAGGCT   1020
GGTTCACTGC ACAGTTCCCA GGGACTTGGG ATGGGTCCTG TGGAGGAGTC CTGGTTTGGT   1080
CCTTCCCTGG AGCACCCACA AGAAGAGAAT GAGCCCAGCC TGCAGAGTAA ACTCCAAGAC   1140
GAAGCCAACT ACCATCTTTA TGGCAGCCGC ATGGACAGGC AGACGAAACA GCAGCCCAGA   1200
CAGAATGTGG CTTACAACAG AGAGGAGGAA AGGAGACGCA GGGTCTCCCA TGACCCTTTT   1260
GCACAGCAAA GACCTTACGA GAATTTTCAG AATACAGAGG GAAAAGGCAC TGTTTATTCC   1320
AGTGCAGCCA GTCATGGTAA TGCAGTGCAC CAGCCATCAG GGCTCACCAG CCAACCTCAA   1380
GTACTGTATC AGAACAATGG ATTATATAGC TCACATGGCT TTGGAACAAG ACCACTGGAT   1440
CCAGGAACAG CAGGTCCCAG AGTTTGGTAC AGGCCAATTC CAAGTCATAT GCCTAGTCTG   1500
CATAATATCC CAGTGCCTGA GACCAACTAT CTAGGAAATT CTCCCACCAT GCCATTCAGC   1560
TCCTTGCCAC CAACAGATGA ATCTATAAAA TATACCATAT ACAATAGTAC TGGCATTCAG   1620
ATTGGAGCCT ACAATTATAT GGAGATTGGT GGGACGAGTT CATCACTACT AGACAGCACA   1680
AATACGAACT TCAAAGAAGA GCCAGCTGCT AAGTACCAAG CTATCTTTGA TAATACCACT   1740
AGTCTGACGG ATAAACACCT GGACCCAATC AGGGAAAATC TGGGAAAGCA CTGGAAAAAC   1800
TGTGCCCGTA AACTGGGCTT CACACAGTCT CAGATTGATG AAATTGACCA TGACTATGAG   1860
CGAGATGGAC TGAAAGAAAA GGTTTACCAG ATGCTCCAAA AGTGGGTGAT GAGGGAAGGC   1920
ATAAAGGGAG CCACGGTGGG GAAGCTGGCC CAGGCGCTCC ACCAGTGTTC CAGGATCGAC   1980
CTTCTGAGCA GCTTGATTTA CGTCAGCCAG AACTAACCCT GGATGGGCTA CGGCAGCTGA   2040
AGTGGACGCC TCACTTAGTG GATAACCCCA GAAAGTTGGC TGCCTCAGAG CATTCAGAAT   2100
TCTGTCCTCA CTGATAGGGG TTCTGTGTCT GCAGAAA                            2137
```

( 2 ) INFORMATION FOR SEQ ID NO:17:

( i ) SEQUENCE CHARACTERISTICS:
    ( A ) LENGTH: 671 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:17:

```
Met Gln Pro Asp Met Ser Leu Asn Val Ile Lys Met Lys Ser Ser Asp
  1               5                  10                  15

Phe Leu Glu Ser Ala Glu Leu Asp Ser Gly Gly Phe Gly Lys Val Ser
             20                  25                  30

Leu Cys Phe His Arg Thr Gln Gly Leu Met Ile Met Lys Thr Val Tyr
         35                  40                  45

Lys Gly Pro Asn Cys Ile Glu His Asn Glu Ala Leu Leu Glu Glu Ala
     50                  55                  60

Lys Met Met Asn Arg Leu Arg His Ser Arg Val Val Lys Leu Leu Gly
 65                  70                  75                  80

Val Ile Ile Glu Glu Gly Lys Tyr Ser Leu Val Met Glu Tyr Met Glu
                 85                  90                  95

Lys Gly Asn Leu Met His Val Leu Lys Ala Glu Met Ser Thr Pro Leu
            100                 105                 110

Ser Val Lys Gly Arg Ile Ile Leu Glu Ile Ile Glu Gly Met Cys Tyr
        115                 120                 125
```

-continued

| | | | | | | | | | | | | | | |
|---|---|---|---|---|---|---|---|---|---|---|---|---|---|---|
| Leu | His | Gly | Lys | Gly | Val | Ile | His | Lys | Asp | Leu | Lys | Pro | Glu | Asn | Ile |
| | 130 | | | | 135 | | | | 140 | | | | | | |
| Leu | Val | Asp | Asn | Asp | Phe | His | Ile | Lys | Ile | Ala | Asp | Leu | Gly | Leu | Ala |
| 145 | | | | | 150 | | | | 155 | | | | | | 160 |
| Ser | Phe | Lys | Met | Trp | Ser | Lys | Leu | Asn | Asn | Glu | Glu | His | Asn | Glu | Leu |
| | | | | 165 | | | | | 170 | | | | | 175 | |
| Arg | Glu | Val | Asp | Gly | Thr | Ala | Lys | Lys | Asn | Gly | Gly | Thr | Leu | Tyr | Tyr |
| | | | 180 | | | | | 185 | | | | | 190 | | |
| Met | Ala | Pro | Glu | His | Leu | Asn | Asp | Val | Asn | Ala | Lys | Pro | Thr | Glu | Lys |
| | | 195 | | | | | 200 | | | | 205 | | | | |
| Ser | Asp | Val | Tyr | Ser | Phe | Ala | Val | Val | Leu | Trp | Ala | Ile | Phe | Ala | Asn |
| | 210 | | | | | 215 | | | | | 220 | | | | |
| Lys | Glu | Pro | Tyr | Glu | Asn | Ala | Ile | Cys | Glu | Gln | Gln | Leu | Ile | Met | Cys |
| 225 | | | | | 230 | | | | | 235 | | | | | 240 |
| Ile | Lys | Ser | Gly | Asn | Arg | Pro | Asp | Val | Asp | Asp | Ile | Thr | Glu | Tyr | Cys |
| | | | | 245 | | | | | 250 | | | | | 255 | |
| Pro | Arg | Glu | Ile | Ile | Ser | Leu | Met | Lys | Leu | Cys | Trp | Glu | Ala | Asn | Pro |
| | | | 260 | | | | | 265 | | | | | 270 | | |
| Glu | Ala | Arg | Pro | Thr | Phe | Pro | Gly | Ile | Glu | Glu | Lys | Phe | Arg | Pro | Phe |
| | | 275 | | | | | 280 | | | | | 285 | | | |
| Tyr | Leu | Ser | Gln | Leu | Glu | Glu | Ser | Val | Glu | Glu | Asp | Val | Lys | Ser | Leu |
| | 290 | | | | | 295 | | | | | 300 | | | | |
| Lys | Lys | Glu | Tyr | Ser | Asn | Glu | Asn | Ala | Val | Val | Lys | Arg | Met | Gln | Ser |
| 305 | | | | | 310 | | | | | 315 | | | | | 320 |
| Leu | Gln | Leu | Asp | Cys | Val | Ala | Val | Pro | Ser | Ser | Arg | Ser | Asn | Ser | Ala |
| | | | | 325 | | | | | 330 | | | | | 335 | |
| Thr | Glu | Gln | Ala | Gly | Ser | Leu | His | Ser | Ser | Gln | Gly | Leu | Gly | Met | Gly |
| | | | 340 | | | | | 345 | | | | | 350 | | |
| Pro | Val | Glu | Glu | Ser | Trp | Phe | Gly | Pro | Ser | Leu | Glu | His | Pro | Gln | Glu |
| | | 355 | | | | | 360 | | | | | 365 | | | |
| Glu | Asn | Glu | Pro | Ser | Leu | Gln | Ser | Lys | Leu | Gln | Asp | Glu | Ala | Asn | Tyr |
| | 370 | | | | | 375 | | | | | 380 | | | | |
| His | Leu | Tyr | Gly | Ser | Arg | Met | Asp | Arg | Gln | Thr | Lys | Gln | Gln | Pro | Arg |
| 385 | | | | | 390 | | | | | 395 | | | | | 400 |
| Gln | Asn | Val | Ala | Tyr | Asn | Arg | Glu | Glu | Arg | Arg | Arg | Arg | Val | Ser | |
| | | | | 405 | | | | | 410 | | | | | 415 | |
| His | Asp | Pro | Phe | Ala | Gln | Gln | Arg | Pro | Tyr | Glu | Asn | Phe | Gln | Asn | Thr |
| | | | 420 | | | | | 425 | | | | | 430 | | |
| Glu | Gly | Lys | Gly | Thr | Val | Tyr | Ser | Ser | Ala | Ala | Ser | His | Gly | Asn | Ala |
| | | 435 | | | | | 440 | | | | | 445 | | | |
| Val | His | Gln | Pro | Ser | Gly | Leu | Thr | Ser | Gln | Pro | Gln | Val | Leu | Tyr | Gln |
| | 450 | | | | | 455 | | | | | 460 | | | | |
| Asn | Asn | Gly | Leu | Tyr | Ser | Ser | His | Gly | Phe | Gly | Thr | Arg | Pro | Leu | Asp |
| 465 | | | | | 470 | | | | | 475 | | | | | 480 |
| Pro | Gly | Thr | Ala | Gly | Pro | Arg | Val | Trp | Tyr | Arg | Pro | Ile | Pro | Ser | His |
| | | | | 485 | | | | | 490 | | | | | 495 | |
| Met | Pro | Ser | Leu | His | Asn | Ile | Pro | Val | Pro | Glu | Thr | Asn | Tyr | Leu | Gly |
| | | | 500 | | | | | 505 | | | | | 510 | | |
| Asn | Ser | Pro | Thr | Met | Pro | Phe | Ser | Ser | Leu | Pro | Pro | Thr | Asp | Glu | Ser |
| | | 515 | | | | | 520 | | | | | 525 | | | |
| Ile | Lys | Tyr | Thr | Ile | Tyr | Asn | Ser | Thr | Gly | Ile | Gln | Ile | Gly | Ala | Tyr |
| | 530 | | | | | 535 | | | | | 540 | | | | |
| Asn | Tyr | Met | Glu | Ile | Gly | Gly | Thr | Ser | Ser | Ser | Leu | Leu | Asp | Ser | Thr |
| 545 | | | | | 550 | | | | | 555 | | | | | 560 |

```
Asn Thr Asn Phe Lys Glu Glu Pro Ala Ala Lys Tyr Gln Ala Ile Phe
                565                 570                 575

Asp Asn Thr Thr Ser Leu Thr Asp Lys His Leu Asp Pro Ile Arg Glu
            580                 585                 590

Asn Leu Gly Lys His Trp Lys Asn Cys Ala Arg Lys Leu Gly Phe Thr
        595                 600                 605

Gln Ser Gln Ile Asp Glu Ile Asp His Asp Tyr Glu Arg Asp Gly Leu
    610                 615                 620

Lys Glu Lys Val Tyr Gln Met Leu Gln Lys Trp Val Met Arg Glu Gly
625                 630                 635                 640

Ile Lys Gly Ala Thr Val Gly Lys Leu Ala Gln Ala Leu His Gln Cys
            645                 650                 655

Ser Arg Ile Asp Leu Leu Ser Ser Leu Ile Tyr Val Ser Gln Asn
            660                 665                 670
```

( 2 ) INFORMATION FOR SEQ ID NO:18:

( i ) SEQUENCE CHARACTERISTICS:
        ( A ) LENGTH: 103 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:18:

```
Ser Arg His Gln Ala Ile Phe Asp Asn Thr Thr Ser Leu Thr Asp Glu
1               5                   10                  15

His Leu Asn Pro Ile Arg Glu Asn Leu Gly Arg Gln Trp Lys Asn Cys
            20                  25                  30

Ala Arg Lys Leu Gly Phe Thr Glu Ser Gln Ile Asp Glu Ile Asp His
            35                  40                  45

Asp Tyr Glu Arg Asp Gly Leu Lys Glu Lys Val Tyr Gln Met Leu Gln
        50                  55                  60

Lys Trp Leu Met Arg Glu Gly Thr Lys Gly Ala Thr Val Gly Lys Leu
65                  70                  75                  80

Ala Gln Ala Leu His Gln Cys Cys Arg Ile Asp Leu Leu Asn His Leu
                85                  90                  95

Ile Leu Arg Ala Ser Gln Ser
            100
```

( 2 ) INFORMATION FOR SEQ ID NO:19:

( i ) SEQUENCE CHARACTERISTICS:
        ( A ) LENGTH: 102 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:19:

```
Ala Lys Tyr Gln Ala Ile Phe Asp Asn Thr Thr Ser Leu Thr Asp Lys
1               5                   10                  15

His Leu Asp Pro Ile Arg Glu Asn Leu Gly Lys His Trp Lys Asn Cys
            20                  25                  30

Ala Arg Lys Leu Gly Phe Thr Gln Ser Gln Ile Asp Glu Ile Asp His
            35                  40                  45

Asp Tyr Glu Arg Asp Gly Leu Lys Glu Lys Val Tyr Gln Met Leu Gln
        50                  55                  60
```

```
Lys Trp Val Met Arg Glu Gly Ile Lys Gly Ala Thr Val Gly Lys Leu
 65              70                  75                  80

Ala Gln Ala Leu His Gln Cys Ser Arg Ile Asp Leu Leu Ser Ser Leu
                 85                  90                  95

Ile Tyr Val Ser Gln Asn
                100
```

(2) INFORMATION FOR SEQ ID NO:20:

(i) SEQUENCE CHARACTERISTICS:
        (A) LENGTH: 106 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:20:

```
Ser Lys Tyr Ile Pro Arg Ile Ala Glu Asp Met Thr Ile Gln Glu Ala
 1               5                  10                  15

Lys Lys Phe Ala Arg Glu Asn Asn Ile Lys Glu Gly Lys Ile Asp Glu
                20                  25                  30

Ile Met His Asp Ser Ile Gln Asp Thr Ala Glu Gln Lys Val Gln Leu
                35                  40                  45

Leu Leu Cys Trp Tyr Gln Ser His Gly Lys Ser Asp Ala Tyr Gln Asp
         50                  55                  60

Leu Ile Lys Gly Leu Lys Lys Ala Glu Cys Arg Arg Thr Leu Asp Lys
 65              70                  75                  80

Phe Gln Asp Met Val Gln Lys Asp Leu Gly Lys Ser Thr Pro Asp Thr
                 85                  90                  95

Gly Asn Glu Asn Glu Gly Gln Cys Leu Glu
                100             105
```

(2) INFORMATION FOR SEQ ID NO:21:

(i) SEQUENCE CHARACTERISTICS:
        (A) LENGTH: 106 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:21:

```
Ser Lys Tyr Ile Thr Thr Ile Ala Gly Val Met Thr Leu Ser Gln Val
 1               5                  10                  15

Lys Gly Phe Val Arg Lys Asn Gly Val Asn Glu Ala Lys Ile Asp Glu
                20                  25                  30

Ile Lys Asn Asp Asn Val Gln Asp Thr Ala Glu Gln Lys Val Gln Leu
                35                  40                  45

Leu Arg Asn Trp His Gln Leu His Gly Lys Lys Glu Ala Tyr Asp Thr
         50                  55                  60

Leu Ile Lys Asp Leu Lys Lys Ala Asn Leu Cys Thr Leu Ala Glu Lys
 65              70                  75                  80

Ile Gln Thr Ile Ile Leu Lys Asp Ile Thr Ser Asp Ser Glu Asn Ser
                 85                  90                  95

Asn Phe Arg Asn Glu Ile Gln Ser Leu Val
                100             105
```

(2) INFORMATION FOR SEQ ID NO:22:

(i) SEQUENCE CHARACTERISTICS:
(A) LENGTH: 114 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:22:

| Lys | Trp | Glu | Asp | Ser | Ala | His | Pro | Gln | Arg | Pro | Asp | Asn | Ala | Asp | Leu |
|---|---|---|---|---|---|---|---|---|---|---|---|---|---|---|---|
| 1 | | | | 5 | | | | | 10 | | | | | 15 | |
| Ala | Ile | Leu | Tyr | Ala | Val | Val | Asp | Gly | Val | Pro | Pro | Ala | Arg | Trp | Lys |
| | | | 20 | | | | | 25 | | | | | 30 | | |
| Glu | Phe | Met | Arg | Phe | Met | Gly | Leu | Ser | Glu | His | Glu | Ile | Glu | Arg | Leu |
| | | 35 | | | | | 40 | | | | | 45 | | | |
| Glu | Met | Gln | Asn | Gly | Arg | Cys | Leu | Arg | Glu | Ala | Gln | Tyr | Ser | Met | Leu |
| | 50 | | | | | 55 | | | | | 60 | | | | |
| Glu | Ala | Trp | Arg | Arg | Arg | Thr | Pro | Arg | His | Glu | Asp | Thr | Leu | Glu | Val |
| 65 | | | | | 70 | | | | | 75 | | | | | 80 |
| Val | Gly | Leu | Val | Leu | Ser | Lys | Met | Asn | Leu | Ala | Gly | Cys | Leu | Glu | Asn |
| | | | | 85 | | | | | 90 | | | | | 95 | |
| Ile | Leu | Glu | Ala | Leu | Arg | Asn | Pro | Ala | Pro | Ser | Ser | Thr | Thr | Arg | Leu |
| | | | 100 | | | | | 105 | | | | | 110 | | |
| Pro | Arg | | | | | | | | | | | | | | |

(2) INFORMATION FOR SEQ ID NO:23:

(i) SEQUENCE CHARACTERISTICS:
(A) LENGTH: 117 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:23:

| Lys | Trp | Glu | Asp | Ser | Ala | His | Lys | Pro | Gln | Ser | Leu | Asp | Thr | Asp | Asp |
|---|---|---|---|---|---|---|---|---|---|---|---|---|---|---|---|
| 1 | | | | 5 | | | | | 10 | | | | | 15 | |
| Pro | Ala | Thr | Leu | Tyr | Ala | Val | Val | Glu | Asn | Val | Pro | Pro | Leu | Arg | Trp |
| | | | 20 | | | | | 25 | | | | | 30 | | |
| Lys | Glu | Phe | Val | Arg | Arg | Leu | Gly | Leu | Ser | Asp | His | Glu | Ile | Asp | Arg |
| | | 35 | | | | | 40 | | | | | 45 | | | |
| Leu | Glu | Leu | Gln | Asn | Gly | Arg | Cys | Leu | Arg | Glu | Ala | Gln | Tyr | Ser | Met |
| | 50 | | | | | 55 | | | | | 60 | | | | |
| Leu | Ala | Thr | Trp | Arg | Arg | Arg | Thr | Pro | Arg | Arg | Glu | Ala | Thr | Leu | Glu |
| 65 | | | | | 70 | | | | | 75 | | | | | 80 |
| Leu | Leu | Gly | Arg | Val | Leu | Arg | Asp | Met | Asp | Leu | Leu | Gly | Cys | Leu | Glu |
| | | | | 85 | | | | | 90 | | | | | 95 | |
| Asp | Ile | Glu | Glu | Ala | Leu | Cys | Cys | Gly | Pro | Ala | Ala | Leu | Pro | Pro | Ala |
| | | | 100 | | | | | 105 | | | | | 110 | | |
| Pro | Ser | Leu | Leu | Arg | | | | | | | | | | | |
| | | | 115 | | | | | | | | | | | | |

CELL DEATH PROTEIN

STATEMENT AS TO FEDERALLY SPONSORED RESEARCH

Work on this invention was supported, in part, with funds from the United States government (NIH grant DK43031). The government therefore has certain rights in the invention.

FIELD OF THE INVENTION

This invention relates to recombinant DNA, proteins encoded by recombinant DNA, and screening methods for discovery of compounds with pharmacological activity.

BACKGROUND OF THE INVENTION

Regulated (or "programmed") cell death is essential for the orderly development of metazoan organisms and is crucial to the proper functioning of the immune system in higher vertebrates (Wyllie et al., Int. Rev. Cytol. 68:251–306, 1980). The most common morphologic expression of programmed cell death is apoptosis, characterized by cell shrinkage, zeiosis, or blebbing, of the plasma membrane, and nuclear collapse and fragmentation of the nuclear chromatin, at intranucleosomal sites, due to activation of an endogenous nuclease (Clement et al., J. Exp. Med. 180:557, 1994). Apoptosis is involved in morphological development, precise regulation of cell numbers, and as a defense mechanism to remove unwanted, and potentially dangerous cells, such as self-reactive lymphocytes, cells infected by viruses, and tumor cells. See, e.g., Steller, Science 267:1445, 1995; Thompson, Science 267:1456, 1995. Diseases associated with increased apoptosis include AIDS, neurodegenerative disorders (e.g., Alzheimer's disease, Parkinson's disease, amyotrophic lateral sclerosis, retinitis pigmentosa), aplastic anemia, ischemic injury (e.g., myocardial infarction, stroke, reperfusion injury), and toxin-induced (e.g., alcohol induced) liver disease.

An important mediator of immunologically relevant cell death is the Fas antigen/APO-1 (also known as CD95) ("Fas/APO-1"), originally identified as the target of monoclonal antibodies that could kill multiple cell types (Trauth et al., Science 245:301, 1989; Yonehara et al., J. Exp. Med., 169:1747, 1989). Cloning of cDNA, followed by sequence analysis (Itoh et al., Cell 66:233, 1991; Watanabe-Fukanaga et al., J. Immunol. 148:1274, 1992a; Oehm et al., J. Biol. Chem. 267:10709, 1992) showed Fas/APO-1 to be a member of a family of transmembrane receptors that includes the low affinity nerve growth factor ("NGF") receptor, the tumor necrosis factor receptors ("TNFR1," "TNFR2"), and a variety of immune cell receptors including CD40, OX40, CD40, CD27, and 4-1BB (see, Smith et al., Cell 76:959, 1994). In addition to Fas/APO-1, several members of this family have been shown to regulate or induce cell death, e.g., p55 TNFR (TNFR1) Tartaglia et al., Proc. Natl. Acad. Sci. 88:9292, 1991; Tartaglia et al., Cell 73:213, 1993b) and p75 TNFR (TNFR2) (Heller et al., Cell 70:47, 1992; Heller et al., Cell 73:216, 1993; Clement and Stamenkovic, J. Exp. Med. 180:557, 1994).

Disruption of Fas/APO-1 expression or function in lymphoproliferation ("lpr") mutant mice leads to a progressive lymphadenopathy and an autoimmune syndrome resembling human systemic lupus erythematosis (Watanabe-Fukunaga et al., Nature 356:314, 1992b). The residual cytotoxic activity of T-cells derived from perforin deficient mice is also dependent on the presence of at least one wild type allele of the lpr locus (Kagi et al., Science 265:528, 1994; Kojima et al., Immunity 1:357, 1994; Lowin et al., Nature 370:650, 1994). Thus the ability of Fas/APO-1 to induce cell death is important for the maintenance of at least two immunologic processes in vivo: peripheral tolerance to self (Singer and Abbas, Immunity 1:365, 1994; Crispe, Immunity 1:347, 1994), and calcium-independent T-cell cytotoxicity (Henkart, Immunity 1:343, 1994).

The mechanism by which Fas/APO-1 induces cell death is unknown, but it requires multivalent cross-linking of the receptor (Dhein et al., J. Immunol. 149:3166, 1992) and is facilitated by concurrent inhibition of RNA or protein synthesis in some cell types. Other factors have been reported to modulate Fas/APO-1 activity (Klas et al., Int. Immunol. 5:625, 1993), and, under certain circumstances, Fas is capable of signaling activation rather than death (Alderson et al., J. Exp. Med. 178:2231, 1993). Anti-Fas antibodies and TNF are both capable of signaling cell death in vitro with similar kinetics (Yonehara et al., (supra); Itoh and Nagata, J. Biol. Chem. 268:10932, 1993), and among members of the NGF/TNF receptor family, Fas/APO-1 and TNFR1 share the most significant cytoplasmic homology.

Fas/APO-1 contains sequences required for the cell death response (Itoh and Nagata (supra) 1993). It has been proposed that a "death domain" contained in a region of similarity between Fas/APO-1 and TNFR1 is essential for the initiation of apoptosis by both molecules, perhaps through an interaction with other intracellular proteins (Tartaglia et al., Cell 74:845, 1993).

SUMMARY OF THE INVENTION

We have discovered a protein, designated RIP (for Receptor Interacting Protein), which contains a death domain at its carboxy terminus and a kinase domain at its amino terminus. We have further discovered that RIP interacts with the Fas/APO-1 intracellular domain. Moreover, RIP overexpression in eukaryotic cells leads to apoptosis. The ability of RIP to associate with the Fas/APO-1 intracellular domain, and to promote apoptosis, indicates that it is an important element in the signal transduction machinery mediating programmed cell death.

Accordingly, the invention features an RIP, comprising a death domain in its carboxy terminal region and a kinase domain in its amino terminal region, said RIP being capable of interacting with cellular factors such as the Fas/APO-1 intracellular domain, or the TNFR1 intracellular domain, and said RIP being capable of promoting apoptosis in a eukaryotic cell. The invention also features RIP fragments, e.g., the RIP death domain, capable of interacting with one or more cellular factors and capable of promoting apoptosis.

The invention also features an isolated recombinant DNA molecule encoding an RIP, or encoding a fragment thereof (e.g., the RIP death domain) and a host cell transformed with the recombinant DNA molecule. The transformed host cell is used to express recombinant RIP.

The invention also features anti-RIP antibodies, which are useful as medical diagnostic reagents, as affinity chromatography reagents for isolation of RIP, and as analytical scale laboratory reagents for use in research on the physiology and cell biology of apoptosis.

The invention also features screening assays to identify inhibitors of in vivo binding interactions mediated by the RIP death domain. Isolated RIP, recombinant RIP, or a binding domain thereof, is an essential component of the screening assays of this invention.

The invention also features screening assays to identify inducers of RIP expression and resulting apoptosis.

The invention also features methods of producing, for introduction into a patient undergoing gene therapy, cells that can be induced to undergo apoptosis upon administration of an exogenous agent to the patient.

As used herein, the term "Act-Fas" means a transcriptional activator fusion protein expressed by a library isolate, wherein the activator is fused to a Fas/APO-1 sequence.

As used herein, the term "Act-RIP" means a transcriptional activator fusion protein expressed by a library isolate, wherein the activator is fused to an RIP sequence.

As used herein, the term "apoptosis" means non-necrotic cell death that takes place in metazoan animal cells following activation of an intrinsic cell suicide program. Apoptosis is a normal process in the development and homeostasis of metazoan animals. Apoptosis involves characteristic morphological and biochemical changes, including cell shrinkage, zeiosis, or blebbing, of the plasma membrane, and nuclear collapse and fragmentation of the nuclear chromatin, at intranucleosomal sites, due to activation of an endogenous nuclease.

As used herein, the term "death domain" of RIP means the 98 C-terminal amino acid residues of RIP, which display sequence relatedness to an approximately 90-amino acid residue C-terminal region in Fas/APO-1 and TNFR1.

As used herein, the term "interacting" means specifically associating as a result of 3-dimensional structure; specific non-covalent binding.

As used herein, the term "kinase domain" of RIP means the amino terminal region of RIP (i.e., from a few residues after the N-terminal methionine residue to approximately residue number 300), which has sequence relatedness to known tyrosine kinases and serine/threonine kinases.

Other features and advantages of the invention will be apparent from the following description of the preferred embodiments thereof, and from the claims.

BRIEF DESCRIPTION OF THE DRAWINGS

FIG. 3 is the deduced complete amino acid sequence of murine RIP and a deduced partial human RIP amino acid sequence.

Figure 1:
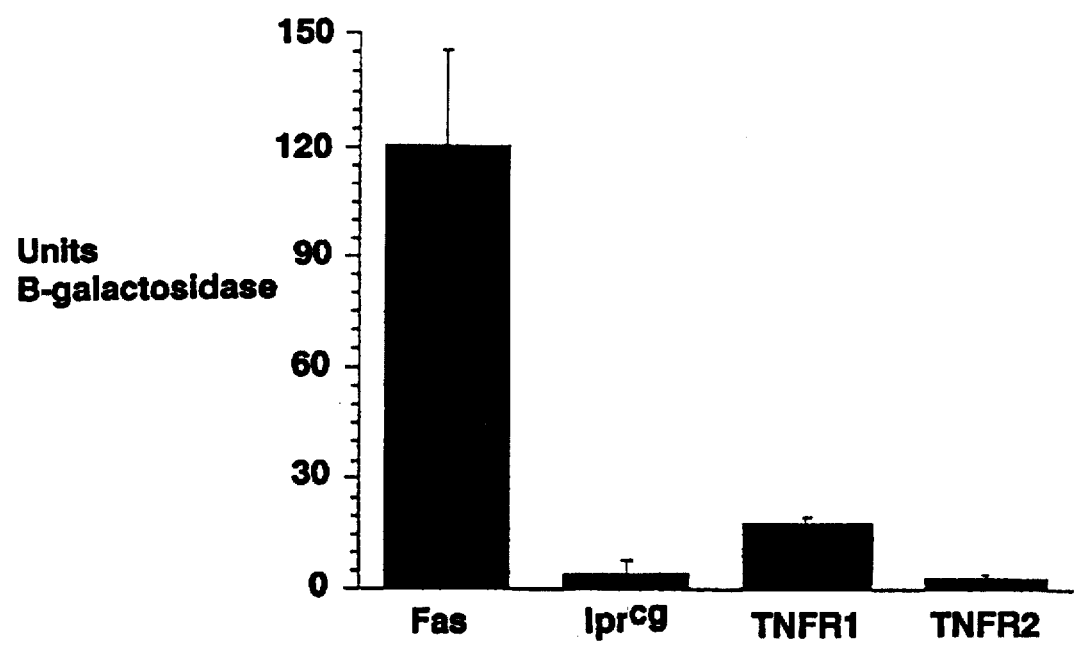
FIG. 1 is a graph summarizing quantitative β-galactosidase assay results. Three colonies from each Act-RIP/LexA-fusion protein pair were used to inoculate a galactose-containing liquid culture. The β-galactosidase activity of lysates prepared from each culture was measured and normalized to the total protein concentration of the lysate. 5 units (nmoles/min/mg protein) represents the limit of detection of β-galactosidase activity in this system.

(B) Deduced polypeptide sequence. The mouse sequence consists of a contiguous open reading frame proceeding from a translational initiation consensus. The human sequence predicted from a cDNA fragment is shown below the mouse; identical residues are indicated by a dash, and gaps indicated by a period. The conserved consensus sequences for casein kinase II (S-X-X-E) and cAMP- or cGMP-dependent protein kinase (R-X-X-S) are overlined.

Figure 4:
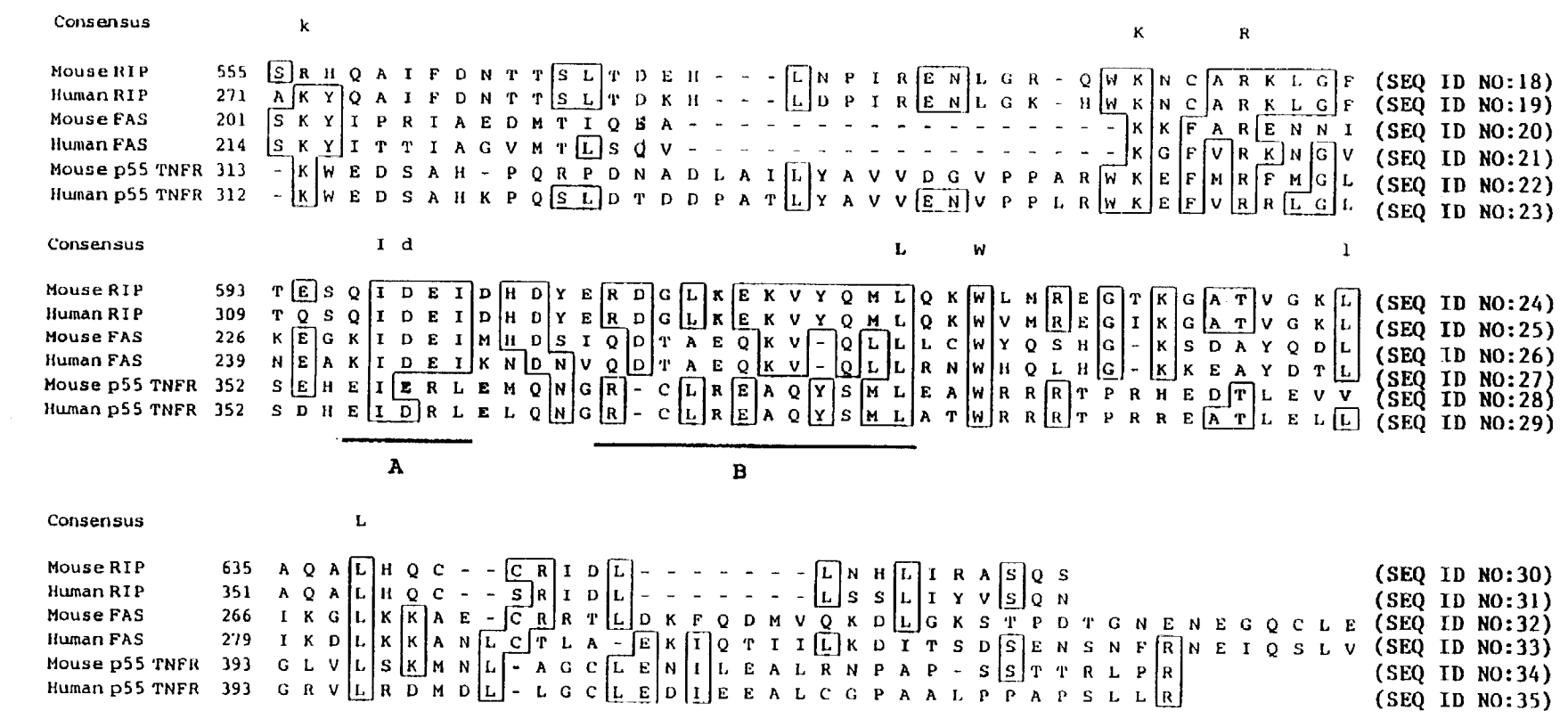

FIG. 4 is the amino acid sequence of the RIP Death Domain. Sequence alignment of the RIP C-terminus with the death domains and carboxyl termini of Fas/APO-1 and TNFR1. Gaps are indicated by dashes. Consensus residues conserved in all six sequences are capitalized, whereas positions at which a charge-conserved residue is found in 1/6 sequences are shown in lower case. Noteworthy charge conservations are bolded. The regions denoted A and B represent two portions of the Fas/APO-1 cytoplasmic domain completely conserved between mouse and human.

DETAILED DESCRIPTION

The present invention provides a novel recombinant protein, designated RIP, and DNA encoding the protein. RIP contains an amino-terminal kinase domain and a carboxy-terminal death domain, through which RIP associates with the Fas/APO-1 intracellular domain, and to a lesser extent, the TNFR1 intracellular domain. RIP appears to be an apoptosis-inducing nonreceptor kinase. Accordingly, RIP appears to be an important element in the signal transduction pathway mediating programmed cell death.

Various diseases, including AIDS, neurodegenerative disorders (e.g., Alzheimer's disease, Parkinson's disease, amyotrophic lateral sclerosis, retinitis pigmentosa), aplastic anemia, ischemic injury (e.g., myocardial infarction, stroke, reperfusion injury), and toxin-induced (e.g., alcohol induced) liver disease, involve abnormal increases in apoptosis. A specific inhibitor of an essential step in the biochemical machinery that mediates apoptosis is needed. Such an inhibitor would be a drug candidate for therapeutic use against apoptosis-associated diseases. Because RIP interaction with (i.e., binding to) intracellular factors appears to be an essential step in triggering apoptosis, inhibitors of RIP binding to intracellular apoptosis factors, e.g., Fas/APO-1 or TNFR1, are potential drug candidates. RIP (or a fragment thereof) is an essential component in any screening method for discovery of such RIP binding inhibitors.

RIP inhibitor screening methods, including cell-free methods and cellular methods, can be used in the practice of this invention. Cellular screening methods within the scope of this invention can involve transient expression vectors or stable transformation. Various RIP inhibitor screening protocols can be designed, according to well-known principles, by one of ordinary skill in the art, once RIP and RIP-encoding DNA are in hand, by virtue of the present invention.

Cell-free screening methods for inhibitors of RIP death domain-mediated binding involve the use of isolated RIP and an RIP interaction partner, e.g., isolated Fas/APO-1 protein, TNFR1, or a polypeptide comprising the appropriate binding domain of one of these proteins. Soluble forms of RIP and RIP interaction partners can be utilized in cell free RIP inhibitor screening protocols. Preferably, however, the cell-free RIP inhibitor screening protocol involves an RIP interaction partner inserted into a biological membrane. Membrane-inserted fusion protein forms of Fas/APO-1, can be produced, for example, using known sequences, according to the methods of Clement et al. (supra).

Preferably, RIP inhibitor screening is carried out in a cellular system, using a reporter strain of cultured mammalian cells, transformed with one or more vectors encoding RIP, and other assay components, as necessary. Preferably, an RIP-encoding sequence is cloned into a recombinant DNA vector, where it is expressed under the control of an inducible promoter, e.g., a heat shock promoter. See, e.g., Wurm et al., Proc. Natl. Acad. Sci. U.S.A. 83:5414, 1986. Following induction of RIP expression, Cell death is measured in experimental treatments involving the presence of an inhibitor candidate, and in appropriate positive and negative controls. Various assays for cell death are known in the art, including the neutral red uptake method (Wallach, J. Immunol. 132:2464, 1984), the crystal violet method (see, e.g., Itoh et al., supra), or microscopic inspection of cells for visual signs of apoptosis.

Because overexpression of RIP can be used to induce apoptotic cell death, RIP is useful as a tool in gene therapy in at least two different ways: (1) to control the number of cells bearing a specific gene; and (2) to act as an anti-tumor agent in forms of cancer therapy that are dependent on the delivery of a lethal gene to neoplastic cells. In both applications, overexpression of RIP to cause apoptotic cell death is preferable to approaches employing death-inducing genes that result in in vivo generation of toxic agents or that interfere with cell cycle progression.

Cell ablation through RIP expression is advantageous because apoptotic death affects both mitotically active and mitotically quiescent cells. In contrast, chemotherapeutic agents and many gene therapy-based treatments for tumors require the target cell to be replicating in order for the treatment to be effective.

RIP genes used in gene therapy are preferably under the control of an exogenously regulatable promoter. An exogenously regulatable promoter is a promoter that can be induced by a specific set of environmental conditions, such as the increase in the concentration of a specific inducer. Examples of exogenously regulatable promoters and inducing conditions include: induction of a metallothionein promoter by zinc ions (Makarove et al., Nucleic Acids Res. 22:1504–1505, 1994), removal of tetracycline, thereby activating a synthetic promoter based on the action of a tetracycline repressor-VP16 chimera (Gossen et al., Proc. Natl. Acad. Sci. U.S.A. 89:5547–5551, 1992), addition of ecdysone (Christopherson et al., Proc. Natl. Acad. Sci. U.S.A. 89:6314–6318, 1992), or the synthetic progesterone antagonist mifepristone (Wang et al., Proc. Natl. Acad. Sci. U.S.A. 91:8180–8184, 1994).

The RIP-encoding DNA of this invention enables one of ordinary skill in the art to produce anti-RIP antibodies. The RIP-encoding DNA is used to construct a vector encoding a fusion protein comprising an RIP moiety and an isolation-facilitating moiety, i.e., a moiety that can be readily isolated from contaminating proteins in an extract from a host cell used to express the fusion protein. A preferred isolation-facilitating moiety is maltose binding protein. DNA encoding maltose binding protein is commercially available. A binding reagent specific for the isolation-facilitating moiety is used for convenient and efficient isolation of the RIP fusion protein. For example, amylose chromatography is preferred for isolation of a fusion protein comprising maltose binding protein moiety. Following isolation, the RIP fusion protein is used to produce RIP-specific antibodies (polyclonal or monoclonal), according to standard methods, described, for example, by Harlow et al., (*Antibodies—A Laboratory Manual*, Cold Spring Harbor Laboratory, 1988).

The anti-RIP antibodies of the invention have several uses. For example, they may be used as reagents for preparation of affinity chromatography media. Once the anti-RIP antibodies of this invention are in hand, preparation of RIP affinity chromatography media can be carried out according to conventional methods (see, e.g., Harlow et al., supra), using commercially available reagents. The RIP-specific affinity chromatography media can be used to isolate full-length RIP from natural sources or from host cells transformed with recombinant DNA encoding RIP.

The anti-RIP antibodies of the invention are also useful as analytical-scale laboratory reagents for research on the physiology and cell biology of apoptosis. For example, immunohistochemical techniques, based on anti-RIP monoclonal antibodies are likely to be valuable tools for embryologists seeking ways to observe the rate and/or distribution of apoptosis in the normal morphological development of metazoan animals.

The anti-RIP antibodies of the invention are also useful as diagnostic immunoassay reagents for measuring RIP levels in tissue samples from patients suspected of having an apoptosis-related disease or abnormality. Information on RIP levels in selected cells or tissues is a useful diagnostic or prognostic indicator in any situation where the rate of programmed cell death is important. The type of tissue sampled for the diagnostic test will vary, depending on the signs and symptoms of the patient and the suspected disease or abnormality.

If the tissue sample is highly homogenous with respect to cell type, it may be preferable to carry out the RIP immunoassay on an extract from a homogenate. Alternatively, it may be preferable to use an immunohistochemical assay involving anti-RIP antibodies. An immunohistochemical assay is preferable when the tissue sample is heterogenous with respect to cell type. An immunohistochemical assay will yield information on the distribution of differing RIP levels in a cross section of tissue, or differing RIP levels in various types of blood cells in a blood sample.

Although inhibitors of RIP binding to intracellular apoptosis factors would be expected to have therapeutic utility only for disease states involving increased apoptosis, information on the level of RIP in a tissue sample would have diagnostic/prognostic utility for any apoptosis-related disease, regardless of whether apoptosis was increased or decreased in that disease. Examples of diseases associated with decreased apoptosis include cancer (in particular, follicular lymphomas, carcinomas with p53 mutations, hormone-dependent tumors, e.g., breast cancer, prostate cancer, ovarian cancer), autoimmune disorders (e.g., systemic lupus erythematosus, immune-mediated glomerulonephritis), viral infections, herpes viruses, poxviruses, adenoviruses).

The anti-RIP antibodies of the present invention can be used in various diagnostic immunoassay formats known in the art. Exemplary immunoassay formats are competitive radioimmunoassay, ELISA, Western blot analysis and microcapillary devices comprising immobilized antibody. See, e.g., Dafforn et al., Clin. Chem. 36:1312, 1990; Li et al., Anal. Biochem. 166:276, 1987; Zuk et al., U.S. Pat. No. 4,435,504; Zuk et al., Clin. Chem. 31:1144, 1985; Tom et al., U.S. Pat. No. 4,366,241; and Clark, PCT published application WO 93/03176.

The RIP-encoding DNA of this invention can be used as an in situ hybridization reagent to assess transcription of RIP genes and observe RIP RNA processing, for diagnostic purposes or research purposes.

The RIP-encoding DNA of this invention can be obtained by screening a transcriptional activator fusion library from the species of interest, by means of a protein interaction system, as was done in the original work on this invention, and which is described in detail, below. Preferably, however, RIP-encoding DNA is obtained through a more direct approach, using nucleotide sequences or amino acid sequence information provided herein.

A general method for cloning a full length human RIP cDNA involves screening a human cDNA library (randomly primed from any tissue) with a probe derived from the 5' region of the murine RIP coding sequence, using a low stringency procedure similar to that described under the "cDNA Cloning" heading, below.

A wide variety of host/expression vector combinations can be employed for expressing RIP-encoding DNA of this invention. The expression of RIP-encoding DNA in a cellular screening assay is preferably in a eukaryotic cell, under the control of eukaryotic expression control sequences. More preferably, the eukaryotic cell is a cultured mammalian cell. If the expression of recombinant RIP-encoding DNA is merely for the production of isolated recombinant RIP, however, a prokaryotic host/expression vector system or a eukaryotic host/expression system can be used.

In the studies leading to the present invention, a yeast two-hybrid screen of a human T-cell cDNA library identified two proteins capable of interacting with the intracellular domain of Fas/APO-1: Fas/APO-1 itself and a novel protein, RIP, containing a death domain and a kinase domain. Neither protein interacts with a humanized variant of the murine lpr$^{cg}$ allele, which confers much the same phenotype on affected mice as does the original lpr allele (Matsuzawa et al., 1990). The finding that the intracellular domain of the lpr$^{cg}$ variant is incapable of interacting with the wild type Fas/APO-1 cytoplasmic domain in yeast suggests that oligomerization of Fas/APO-1 mediated by cytoplasmic sequences may be a prerequisite for activity. However it has not been established whether oligomerization of Fas/APO-1 is necessary for interaction with RIP, or whether the same subdomain exploited for oligomerization is also required for heteromeric association with RIP. The discovery of the Fas-Fas interaction in a library screen is consistent with a recent demonstration that TNFR1 and Fas/APO-1 are capable of both self- and cross-association in yeast (Boldin et al., J. Biol. Chem. 270:387, 1995). The death domain probably mediates such interactions, because work on this invention indicates that RIP can also associate with the intracellular domain of TNFR1 (as well as the intracellular domain of Fas/APO-1).

RIP mRNA is expressed at low levels in all tissues. A pattern of widespread expression has also been observed for Fas/APO-1. In contrast to RIP, however, Fas/APO-1 mRNA is found at higher levels in thymus, liver, lung, and heart. Like Fas/APO-1 mRNA, RIP mRNA is induced in splenocytes after activation with ConA. Although a requirement for RIP in Fas-mediated killing has not been established, coordinate induction of Fas/APO-1 and RIP may contribute to increased susceptibility of T-cells to Fas-mediated cell death following activation.

The N-terminus of RIP contains a kinase domain that has features of both Ser/Thr and Tyr kinases. In the two interacting loops that appear to control hydroxyamino acid recognition (Hubbard et al., Nature 372:746, 1994; Taylor et al., Structure 2:345, 1994), RIP closely resembles a Ser/Thr kinase. In particular, it lacks the Ala-X-Arg or Arg-X-Ala motif in the catalytic loop (subdomain VI) and the Pro-X-X-Trip motif in the P+1 loop (subdomain VIII), both of which are found in all Tyr kinases (see, e.g., Hanks et al., in Meth. Enzymol. 200, Academic Press, at pp. 38–62, 1991).

Other support for the possibility that RIP has either mixed catalytic specificity or Tyr kinase-like regulation with Ser/Thr specificity, comes from the finding that, among known sequences, RIP shows the greatest overall primary sequence similarity to murine lck, a tyrosine kinase of the src family. The relatedness to tyrosine kinases is especially apparent among the framework residues outside the active site which make up the C-terminal, alpha helic-rich substrate-binding lobe. For example, RIP has a tryptophan at position 269 which is present in all Tyr kinases analyzed by Hanks et al. (Science 241:42, 1988), but absent from all Ser/Thr kinases examined, except Mos. The presence of structural motifs from both Tyr and Ser/Thr kinases has also been noted for the soybean kinase GmPK6 (Feng et al., Biochim. Biophys Acta 1172:200, 1993), which shows high global similarity to RIP. Although the exact role of protein kinases in Fas/APO-1 mediated apoptosis is unknown, it appears that the participation of at least one protein tyrosine kinase is required.

In work on this invention, overexpression of RIP resulted in the induction of a cell death program morphologically indistinguishable from apoptosis. Deletion of the C-terminal region of RIP spanning the segment of death domain homology eliminated the apoptotic response, but deletion of the kinase domain did not entirely quench activity.

Although the evidence that RIP binds to Fas/APO-1 in yeast favors a model in which RIP acts directly downstream of Fas/APO-1 in a death pathway, it is also possible that RIP has other actions. For example, the elevation of RIP mRNA in activated T-cells suggests that RIP may be involved in the apoptosis provoked by growth factor deprivation.

Experimental Information

RIP cDNAs

A cDNA library screen for proteins that interact with the intracellular domain of Fas/APO-1 was conducted by using a variation of the yeast interaction system described by Gyuris et al. (Cell 75:791, 1993). The assay system involved a yeast reporter strain containing two separate reporter genes, S. cerevisiae leu-2 and E. coli β-galactosidase coding sequences under the control of a synthetic promoter which contain a Lex-A binding site, and which required a transacting transcriptional activator in order for transcription to occur. A cDNA segment comprising most of the cytoplasmic domain of human Fas/APO-1 (residues 192 to 329 of the Fas precursor) was fused to the 3' end of the coding region for the bacterial repressor LexA, in a yeast expression plasmid, which was used to transform the reporter strain. This Fas/LexA construct encoded a transcriptionally inert fusion protein ("the bait"), capable of specific binding at the LexA binding site in the reporter gene promoters, by virtue of the LexA moiety. The bait-expressing reporter strain was transformed with a transcriptional activator fusion protein library prepared from mRNA isolated from the Jurkat (human T-cell leukemia) cell line, which is known to undergo apoptosis when subjected to treatment with anti-Fas antibody. The transcriptional activator moiety of the library-encoded fusion proteins lacked DNA binding activity. Any transcriptional activator fusion protein with the ability to bind to the Fas/APO-1 intracellular domain, however, would bring the transcriptional activator moiety into proximity with the reporter gene promoter, thereby resulting in transcription of the reporter genes.

Transformants were plated on selective (leucine deficient) plates containing galactose, which induces the GAL1 promoter that directs transcription of the library insert. Leucine prototrophs were transferred to plates containing X-gal and galactose, and colonies giving a dark blue color reaction were recovered and analyzed further.

To test the specificity of the interaction between the candidate interaction partners and Fas/APO-1, the library plasmids were reintroduced into a second strain harboring a LexA-Fas fusion gene (LexA-lpr$^{cg}$) in which the Fas portion had been mutated by substitution of asparagine for valine at position 254 of the Fas/APO-1 precursor sequence. This mutation was expected to exhibit a molecular phenotype similar to that of the murine lpr$^{cg}$ allele, which is formed by substitution of asparagine for isoleucine at the homologous position. None of the candidate plasmids showing evidence of strong interaction with LexA-Fas were capable of interacting with LexA-lpr$^{cg}$ (FIG. 1A; data not shown).

Restriction site and sequence analysis of the cDNA inserts of the candidate clones showed all to be incomplete cDNAs falling into only two classes. One of the inserts encoded the C-terminal residues 222 to 335 of the intracellular domain of Fas/APO-1 itself. The other encoded a protein, designated RIP, which had no overt relationship to previously described polypeptides.

The specificity of the interaction partners was further tested by using the library plasmids to transform yeast harboring expression plasmids encoding LexA fusions with intracellular domains of various cell surface receptors. Although no interaction was detected in most cases, weak interaction was detected following introduction of the yeast plasmid encoding Act-RIP into strains harboring LexA-TNFR1 intracellular domain. By contrast, no activity was seen when Act-RIP was introduced into strains harboring LexA-TNFR2 intracellular domain. Yeast transformed with Act-Fas displayed promoter activity in strains harboring LexA-Fas intracellular domain, but showed no activity in strains harboring any other LexA-intracellular domain.

To measure this effect more precisely, β-galagalactosidase assays were performed on lysates of yeast harboring various pairs of LexA-intracellular domain and Act-RIP. Lysates from yeast bearing LexA-Fas and Act-RIP contained about 30 to 40 fold more β-galactosidase activity than strains bearing Act-RIP and either LexA-lpr$^{cg}$ or LexA-TNFR2 (FIG. 1). Lysates prepared from yeast harboring LexA-TNFR1 and Act-RIP expressed β-galactosidase activity at about 10% of the level seen in lysates prepared from yeast bearing LexA-Fas and Act-RIP (FIG. 1).

One explanation for the failure to detect an interaction between Act-RIP and LexA-lpr$^{cg}$ or LexA-TNFR2 could have been that the LexA fusion proteins were poorly expressed. To address this possibility, a portion of each lysate used to measure enzyme activity was subjected to gel electrophoresis and blot transfer, followed by detection with anti-LexA antiserum. LexA fusion proteins of the appropriate size were detected in each of the lysates and both the LexA-lpr$^{cg}$ and LexA-TNFR2 fusion proteins were found to be more abundantly expressed than LexA-Fas or LexA-TNFR1 (data not shown), making it unlikely that failure to detect interaction in vivo could be attributed to degradation or inadequate synthesis of the LexA chimeras.

Cloning and Structure of Murine RIP

Because the RIP cDNA insert identified in the two hybrid screen did not encode an open reading frame bearing a consensus translational initiation sequence, additional human cDNA libraries were screened by hybridization for a full length clone. Initially, none were identified, however, and several of the resulting isolates appeared to terminate at approximately the same 5' terminus, suggesting that secondary structure in the mRNA might have prevented extension of the cDNA by reverse transcriptase. (Subsequently, overlapping cDNA clones representing the entire human RIP coding sequence were obtained.) Although the largest clone spanned approximately 1 kb of sequence, preliminary RNA blot hybridizations revealed a transcript of approximately 4.2 kb expressed in cell lines of diverse provenance, including tumors of lymphoid, hepatic, renal, neuronal, cervical, intestinal, muscular and skeletal origin.

Figure 2:
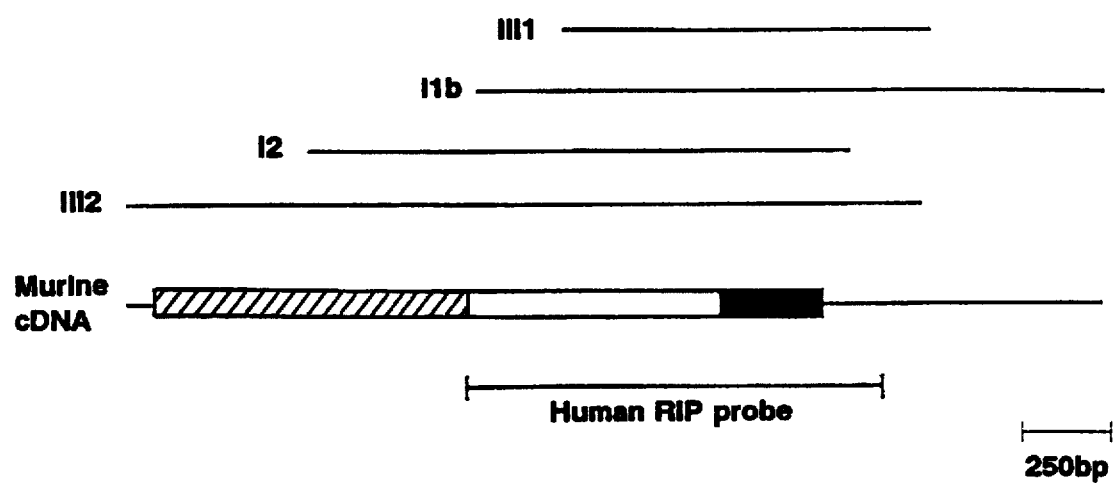
FIG. 2 is a set of genetic maps comparing RIP cDNAs. The inserts of clones isolated from a mouse thymus cDNA library are symbolized as lines above a bar diagram of the composite sequence, which depicts the regions encoding the kinase domain (hatched box), the death domain (black box), and a region of unknown function predicted to have high α-helical content (unshaded). Also shown is the region of human RIP that was used as a probe to isolate murine cDNAs. The original human RIP isolate encompassed sequences encoding the death domain and about 100 residues upstream.
Figure 3:
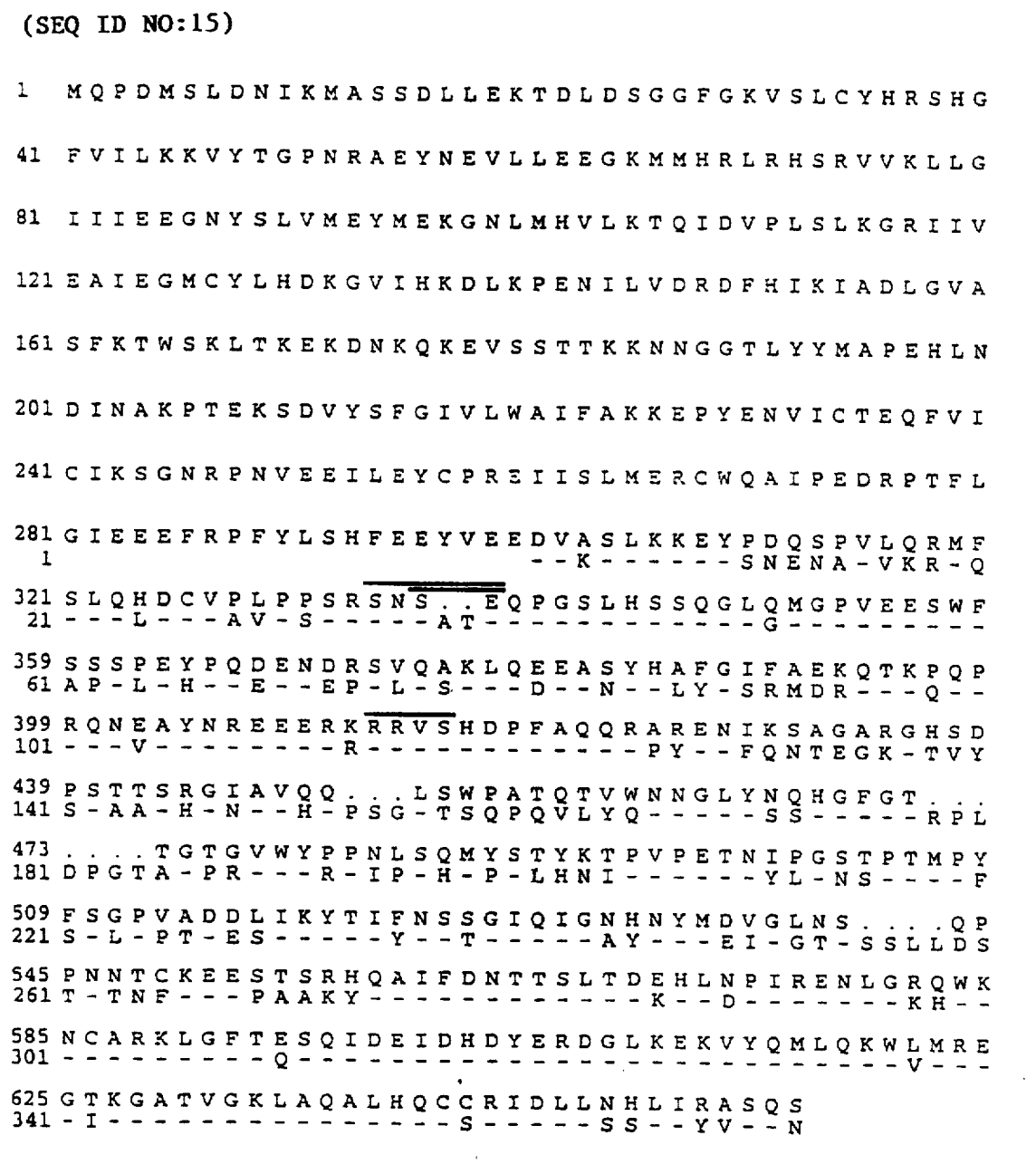

To isolate a full length murine RIP clone, the human RIP coding sequence was used to probe a mouse thymus cDNA library. Four distinct overlapping clones were identified, ranging in size from 1 kb to 2.4 kb, as shown in FIG. 2. Restriction analysis and sequencing revealed that one of these clones, III2, extended further 5' than the others. The 2.3 kb insert of III2 contains a 1968 nucleotide open reading frame beginning with a translational initiation consensus sequence and predicting a polypeptide of 656 amino acids (SEQ ID NO:15) with $M_r$ of 74,000 (FIG. 3). The nucleotide sequence of a full-length murine RIP cDNA is (SEQ ID NO:14).

The amino terminal region of RIP bears an extended homology to protein kinases that begins a few residues after the presumptive initiating methionine and extends to the vicinity of residue 300. Quantitative sequence comparisons based on a word match algorithm (Altshul et al., J. Mol. Biol. 215:403, 1990) predict that this domain is most similar overall to the tyrosine subclass of protein kinases, with the highest relatedness seen to the mouse lck gene product (Marth et al., Cell 43:393, 1985). However in the key subdomains that discriminate most closely between tyrosine and serine/threonine substrate specificity, the HKDLKPEN motif of the catalytic loop (kinase subdomain VI) and the GTLYYMAPE sequence of the P+1 loop (kinase subdomain VIII), RIP appears to match the serine/threonine family consensus (Hanks et al., in Methods in Enzymology vol. 200, (Hunter et al., eds.), Academic Press, pp. 38–62, 1988; Taylor et al.; supra).

The sequence predicted by one of the human cDNA fragments consists of 375 amino acids corresponding to the region just C-terminal to the kinase domain of murine RIP, and shares 67% sequence identity with the murine sequence over this length. Within this portion, the first 270 amino acids following the kinase domain have no striking homology to other proteins, although a small subdomain within this portion is highly conserved between mouse and human proteins (residues 391 to 427 of the murine sequence) and has a relatively high representation of Arg (R), Gln (Q) and Glu (E) (18/37 residues in both sequences). The sequence of this region is similar to portions of the trichohyalin family of hair structural proteins, which contain RQE-rich repeats that form highly stabilized alpha helices (Lee et al., J. Biol. Chem. 268:12164, 1993).

Complete Human RIP Coding Sequence

Subsequent to the cloning and sequencing of a full-length murine RIP cDNA (SEQ ID NO:14), a complete human RIP coding sequence was obtained from sequence analysis of multiple overlapping partial cDNAs. A complete human RIP coding sequence is (SEQ ID NO:16). The deduced amino acid sequence of a full-length human RIP is (SEQ ID NO:17).

RIP C-terminus Death Domain Homology

The remaining 98 C-terminal amino acids share 87% sequence identity between mouse and human RIP, suggesting they subserve some regulatory function (FIG. 3). Comparable domains of approximately 90 residues close to the C-termini of Fas/APO-1 and TNFR1 have been shown to play a role in the transduction of apoptotic signals to receptive cells, and have been termed "death domains" for this reason (Tartaglia et al., Cell 74:845, 1993). Pairwise comparisons of the death domain sequences aligned in FIG. 4 showed the highest relatedness between human RIP and human TNFR1 (59% similarity and 30% identity), which are significantly more similar than human Fas/APO-1 and human TNFR1 (42% similarity and 23% identity). The interspecies conservation of the RIP death domain (85% identity between mouse and human) exceeds that of the TNFR1 (68% identity) and Fas/APO-1 (49% identity) death domains.

Constitutive and Inducible Expression of RIP mRNA

Preliminary RNA blot hybridization experiments demonstrated the existence of an RNA species of approximately 3.8 kb in a variety of cell lines. To more precisely assess mRNA abundance in tissues a quantitative ribonuclease protection assay was employed. Use of a labeled antisense RNA probe corresponding to the 3' terminus of the cDNA gave rise to a ribonuclease resistant species of the expected size in all adult tissues tested. An in vitro labeled RNA antisense to the mRNA for the ribosomal large subunit protein L32 was used as an internal standard to allow normalization to the amount of RNA loaded in each lane. Analysis of the protected RNA showed that RIP mRNA levels varied by less than 2–3 fold between most tissues (not shown); lung showed the highest expression, whereas tongue showed the least.

The possibility that RIP mRNA might be regulated as a consequence of activation in T-cells was also explored. Dissociated murine splenocytes were stimulated in vitro with the lectin concanavalin A and total RNA prepared at various times following addition of lectin was analyzed for the presence of RIP sequences by RNA blot analysis. Little or no RIP RNA could be detected in unstimulated splenocytes, but a single 3.6–3.8 kb species appeared in unfractionated splenocytes that had been exposed to lectin for 2 h or longer. Since RIP mRNA is detectable by ribonuclease protection in the spleen as a whole, the inability to detect RIP mRNA in splenocytes treated with ConA for less than 2 h is probably due to the lower sensitivity of RNA blot analysis, although this discrepancy could also have resulted from RIP expression exclusively in the fibrous tissue of the spleen.

Immunodetection of RIP Produced In Vivo

To examine the distribution of RIP protein in vivo, a rabbit antiserum was prepared against a fusion protein consisting of the 250 C-terminal residues of murine RIP fused to *E. coli* maltose binding protein. The antiserum specificity was validated by immunoprecipitation of RIP synthesized in vitro. Following in vitro transcription and translation of the RIP open reading frame, a single labeled product of approximately 74 kD was observed which could be specifically immunoprecipitated with the rabbit antiserum, but not with serum from unimmunized animals. The specificity of the antiserum for RIP was also documented by its inability to immunoprecipitate an irrelevant protein (*P. pyralis* luciferase) similarly translated in vitro. Immunoprecipitation of a lysate of metabolically labeled NIH3T3 cells with the rabbit antiserum revealed the presence of a single protein species with the same molecular mass as that revealed by in vitro translation of RIP.

Detection of RIP in Transiently Transfected BHK Cells

To determine whether RIP protein could have a direct effect on cell viability, BHK cells grown on coverslips were transiently transfected with a epitope-tagged version of RIP (RIP myc). Transfected cells were reacted with anti-RIP antiserum or an anti-myc monoclonal antibody. Weak expression was detected with both antibodies. The pattern of immunoreactivity was heterogeneous, with both diffuse cytoplasmic as well as punctate perinuclear patterns observed. DNA staining with Hoechst 33258 showed that many of the RIP-expressing cells had apoptotic nuclei, a feature not seen when vector or Fas control expression plasmids were used. However, a number of RIP-expressing cells could be found that had normal-appearing nuclei; conversely, apoptotic cells having no detectable RIP staining were also seen.

The concordance of cell death and RIP expression suggested the ability to detect RIPmyc protein might be compromised by the death of the cells in which it was being expressed. To test this, and the possible role of individual RIP domains in apoptosis, two additional epitope-tagged constructs were prepared: one lacking C-terminal sequences, including the death domain (RIPmycΔdeath), and one lacking ~200 amino acids in the kinase domain (RIPmicΔkinase). Both deletion mutants showed greater immunoreactivity with anti-myc antibodies than the full length construct. Only RIPmicΔkinase was detected by the anti-RIP antiserum, as expected from the deletion of its epitope from RIPmicΔdeath.

RIP Overexpression Leads to Cell Death

To determine whether RIP was inducing cell death, we marked the transfected cells by co-transfection with β-galactosidase. Cells were transfected with pairs of expression plasmids encoding RIPmyc and β-galactosidase (Price et al., 1987) at a 1:3 ratio of β-gal plasmid to RIP plasmid. After histochemical detection of β-galactosidase activity, cells transfected with β-gal and RIPmyc expression plasmids were found to contain a large proportion of intensely staining, shrunken blue cells that exhibited membrane blebbing and loss of adherence. By contrast, transfection with β-gal plasmid, either alone or in combination with RIPmicΔdeath plasmid, had no adverse effect upon nuclear morphology and resulted in a predominantly cytoplasmic β-galactosidase staining pattern. Co-transfection of β-gal plasmid with RIPmicΔkinase likewise gave cytoplasmic staining of healthy-appearing cells, although a number of shrunken, blebbed cells were also seen.

To quantify these results, cells from three independent transfections were examined and the morphologically apoptotic blue cells enumerated as a fraction of total blue cells. Over 57 percent of blue cells arising from co-transfection of RIPmyc and the β-gal plasmid showed morphological changes consistent with apoptosis, whereas only 1–2 percent of blue cells that had been transfected with β-gal plasmid alone or in combination with RIPmicΔdeath exhibited such a phenotype. However a consistent low frequency of apoptotic changes was seen in co-transfections involving RIPmicΔkinase, with almost 11 percent of the blue cells appearing to have undergone cell death. The fraction of cells showing morphological changes was positively correlated with the ratio of RIPmyc or RIPmicΔkinase plasmid to β-gal plasmid, so that increasing RIP:β-gal plasmid ratios gave higher percentages of dead blue cells (data not shown).

Plasmid Construction

The yeast interaction system was modified from that described by Gyuris et al. (supra) by engineering the LexA expression plasmid to remove an internal MluI site and to insert MluI and NotI sites downstream from the DNA portion encoding the C-terminus of the gene. The resulting distal polylinker has the site sequence MluI-PmeI-NotI-EcoRI in the frame in which the MluI site encodes Thr and Arg (frame 1).

The DNA encoding receptor cytoplasmic tails were amplified by PCR from cDNA libraries and cloned as MluI-NotI or BssHII-NotI fragments using the following oligonucleotide primers: Fas: 5'-CGCGGGACGC GTAAG-GAAGT ACAGAAAACA TGC-3' (SEQ ID NO:1) and 5'-CGCGGGGCGG CCGCTCTAGA CCAAGCTTTG GATTTC-3' (SEQ ID NO:2); TNFR1: 5' CGCGGGGCGC GCTACCAACG GTGGAAGTCC AAG-3' (SEQ ID NO:3) and 5' CGCGGGGCGG CCGCTGCCCG CAGGGGCGCA GCCTCA-3' (SEQ ID NO:4); and, TNFR2: 5'-CGCGGGACGC GTAAGAAGCC CTTGTGCCTG CAG-3' (SEQ ID NO:5) and 5'-CGCGGGGCGG CCGCTTTAAC TGGGCTTCAT CCC AGC-3' (SEQ ID NO:6).

The Fas/APO-1 cytoplasmic domain used in the library screen diverges at the Glu located five residues prior to the C-terminus, and continues an additional 25 residues through vector sequences to the C-terminus. In all subsequent analyses, these residues were found not to contribute detectably to either Fas-Fas or Fas-RIP interaction.

A mutant Fas bait protein analogous to the lpr$^{cs}$ point mutation was made by mutating the valine at position 254 of human Fas to asparagine, using the following oligonucleotides in a recombinant PCR reaction:

5'-CGAAAGAATG GTAACAATGAA GCC-3' (SEQ ID NO: 7), and

5'-GGCTTCATTG TTACCATTCTT TCG-3' (SEQ ID NO: 8).

In the resulting construct, residues 330 and 331 were also converted from Glu and Ile to Gly and Asn, respectively.

A myc-tagged version of RIP (RIPmyc) was made by digesting RIP clone III2 with TfiI and ligating a HindIII/TfiI adaptor to the 5' end and TfiI/NotI adaptor containing the myc epitope and a stop codon to the 3' end. The sense (#145) and antisense (#146) oligonucleotides comprising the 3' adaptor were as follows:

145: 5'-ATTCGTGCCA GCCAGAGCGG CATGGAG-CAG AAGCTCATCT CAGAAGAAGA CCTCGCG-TAA GC-3' (SEQ ID NO:9), and

146: 5'-GGCCGCTTAC GCGAGGTCTT CTTCT-GAGAT GAGCTTCTGC TCCATGCCGC TCTG-GCTGGC ACG-3' (SEQ ID NO:10).

The resulting insert was cloned into the HindIII and NotI sites of pcDNA I (Invitrogen).

To make RIPmicΔkinase, a PCR reaction was performed using a 5' RIP primer (#160: 5'-CCCAAGCTTG TTG-GAGATTC TGAGCAATC-3' (SEQ ID NO:11)) and an internal kinase domain primer (#161: 5'-CCCGATCTGC AGGTCATGTA AGTCGCACATGCC-3 (SEQ ID NO:12)). The resulting product was cloned into the HindIII and PstI sites of RIPmyc resulting in the deletion of RIP residues 132 to 323.

RIPmicΔdeath was made by PCR, using a T7 primer and a myc-tag-containing primer (#151: 5'-CCCCTCGAGT TAGAGGTCTT CTTCTGAGAT GAGCTTTTGC TCTTTCTTTA AACTTGCCAC-3' (SEQ ID NO: 13)). The amplified RIPmicΔdeath sequence, lacking amino acids 309 to 656, was subcloned as a HindIII/XhoI fragment into a pcDNA I. Myc tags were located at the C-terminus of all proteins, and thus detection of the myc epitope requires translation of the entire cloned sequence. The BAG retrovirus vector encoding β-galacto-sidase has been described (Price et al., Proc. Natl. Acad. Sci. U.S.A. 84:156, 1987).

Yeast Strains and Library Screen

Yeast transformation with library DNA was performed according to the method of Schiestl and Gietz (Curr. Genet. 16:339, 1989). Recipient cells, EGY48/pRB1840 (Gyuris et al, supra) bearing LexA-fusion protein plasmids, were grown overnight in YPAD medium to a density of approximately $10^7$ cells/ml, then diluted in 100 ml of warmed YPAD to a density of $2 \times 10^6$ cells/ml and regrown to $10^7$ cells/mi. The cells were harvested and washed in water, resuspended in 1 ml water, transferred to a sterile microcentrifuge tube and pelleted. The pellet was resuspended in 0.5 ml of 10 mM Tris HCl (pH 7.5), 1 mM EDTA, 0.1M Li acetate, (pH adjusted to 7.5 with acetic acid and passed through 0.2 micron filter). 50 μl of the resulting suspension was mixed with 1 μg of transforming DNA and 50 μg of single stranded salmon sperm DNA, after which 0.3 ml of a solution of 40% polyethylene glycol-4000 in Tris/EDTA/LiOAc was added and mixed thoroughly, followed by incubation at 30° C. with agitation for 30 min. After a heat pulse at 42° C. for 15 min, the cells were pelleted in a microcentrifuge and the pellets resuspended in 1 ml of Tris/EDTA, diluted and plated on selective medium. Library screening and recovery of plasmids was performed as described by Gyuris et al. (supra).

For assessing the interaction of RIP and Fas with other bait proteins, cells of the yeast strain EGY48/pSH18-34, containing eight copies of the LexA operator-lacZ reporter, were transformed with each of the four bait constructs and selected on Ura$^-$His$^-$ glucose plates. These bait strains were subsequently used for transformation of the RIP or Fas library plasmids and plated on Ura$^-$His$^-$Trip$^-$ Xgal plates containing either 2% glucose of 2% galactose/1% raffinose. The LexA-TNFR2 bait strain gave a weak blue color reaction when grown on galactose, indicating spontaneous transcriptional activation by the fusion protein.

β-Galactosidase Assays and Immunoblotting

Assays of crude extracts were carried out as described (Rose et al., 1990). In brief, cells bearing the appropriate bait and interaction plasmid were grown to saturation overnight at 30° C. in minimal Ura$^-$His$^-$Trip$^-$ medium with 2% glucose. The next day, cells were diluted 1:50 into medium containing 2% galactose and 2% raffinose and allowed to grow overnight. Cells were spun and resuspended in breaking buffer (100 mM Tris (pH 8), 20% glycerol (v/v), 1 mM DTT). Half of each suspension was transferred to a separate tube, and PMSF was added to a final concentration of 10 mM. Cells were lysed by vortexing with acid-washed beads, and the resulting lysate was cleared by centrifugation. Enzyme activity was measured by incubating in Z buffer (Miller, Experiments in Molecular Genetics, Cold Spring Harbor Laboratory, 1972) with 0.67 mg/ml o-nitrophenyl-β-D-galactoside substrate. Reactions were stopped with 0.5 ml 1M Na$_2$CO$_3$ when an appropriate level of color had developed. The protein concentrations of the lysates were determined by Bradford assay. Units of β-galactosidase were calculated using the following equation: specific activity (mmoles/min/mg)=(OD$_{420}$.378)/(time(min).vol extract (ml).concentration (mg/ml)).

cDNA Cloning

Additional clones overlapping the primary RIP isolate were sought in two libraries—an expression library prepared in the CDM8 plasmid vector using mRNA isolated from the human cytolytic T-cell line WH3, and from a commercially available human leukocyte library in lambda phage (Clontech; HL1169a). Both libraries were screened by filter replica hybridization, using radiolabeled probes derived from the insert isolated by interaction screening, as well as from subsequent inserts identified by hybridization.

To isolate murine RIP cDNA clones, 1.2 kb of human RIP sequence was subcloned into two halves and each fragment used to probe genomic DNA blots containing mouse and human DNA to optimize conditions for cross-species hydrization. A commercially available oligo(dT)-primed mouse thymus cDNA library (Stratagene) from a (C57B1/ 6×CBA)F$_1$ mouse was plated out, and $10^6$ plaques were screened using each of the human fragments on duplicate Genescreen filters (DuPont). Probes were synthesized using the random hexamer method Feinberg et al., Anal. Biochem. 132:6, 1983). Hybridization conditions were 5×SSPE, 10×Denhardts, 2% SDS, 0.1 mg/ml herring sperm DNA at 55° C. overnight. Filters were washed in 2×SSC, 0.1% SDS at 55° C. with several changes over 1 h. Plaque purified phage were isolated with three rounds of screening (Sambrook et al.; supra), and in vivo excision carried out using Exassist phage and SOLR™ recipient cells (Stratagene). Seven independent clones were isolated, and they fell into the four classes shown in FIG. 2. The coding sequence of RIP was obtained as a composite from the cDNA clones sequenced on both strands using Sequenase T7 polymerase (U.S. Biochemical). Several nucleotide polymorphisms were detected between the multiple clones, only one of which resulted in an amino acid difference: a Thr to Ile at position 473. Sequence comparisons were done with Genetics Computer Group, Inc. or MegAlign (DNAStar, Inc.) software using default parameters.

RNAse Protections and RNA Blot Hybridization

Tissue RNA samples were prepared from wild type FVB mice (Taconic) by guanidinium thiocyanate lysis and centrifugation through a CsCl cushion (Chirgwin et al., Biochemistry 18:5294, 1979). An antisense probe for RIP made from cDNA clone III1, linearized with SpeI, was synthesized using T7 polymerase with an in vitro transcription kit (Stratagene), with the addition of 20 µM cold rUTP and 100 µCi $^{32}$P-UTP (New England Nuclear). The ribosomal L32 probe was synthesized from an XbaI-linearized template at one tenth the specific activity of the RIP probe. The use of L32 as an internal control for RNA loading has been described elsewhere (Shen and Leder, Proc. Natl. Acad. Sci. U.S.A., 89:8240, 1992). As expected, the in vitro transcription products were slightly larger than the protected fragments of 525 and 279 nucleotides, respectively. After removal of the DNA template with DNAseI, probes were purified using an ultrafree-MC 30,000 retention filter (Millipore). A sample (2×10$^5$ cpm) of the RIP probe and a sample of L32 (2×10$^4$ cpm) were mixed with 10 µg of RNA from each tissue or 50 µg of tRNA and allowed to hybridize in PIPES buffer with 50% formamide overnight at 50° C. Following this incubation, unhybridized RNA was digested with RNAse A (40 µg/ml) and RNAse $T_1$ (1.3 µg/ml) at 37° C. for 15 min. Samples were extracted with phenol/chloroform once, ethanol precipitated, washed, and boiled for 3 min before loading on a 6% polyacrylamide gel. After electrophoresis, gels were dried and exposed and radioactivity was quantitated with the aid of a Molecular Dynamics Phosphorimager.

For measuring RIP in activated T-cells, spleens were removed from adult animals and dissociated using a stainless steel mesh. Cells (~10$^7$ per timepoint) were exposed to ConA (10 µg/ml) for 0–4.5 h, and RNA prepared as described above. Approximately 8 µg of total RNA from each sample was loaded on a 0.9% agarose/4% formaldehyde gel, electrophoresed in 20 mM MOPS, 5 mM sodium acetate, 1 mM EDTA, and transferred to nylon filters (GeneScreen, DuPont) by capillary transfer (Sambrook et al., supra). Sizes were estimated using a molecular weight standard (Gibco BRL). The blot was hybridized with either an RIP probe corresponding to the C-terminal half of the protein (cDNA III1) or with a probe detecting ribosomal 28S RNA. Hybridization was allowed to proceed overnight in 40% formamide, 4×SSC, 10% dextran sulfate, 7 mM Tris (pH 7.6), and 20 µg/ml salmon sperm DNA at 42° C. The blots were then washed at 50° C. in 1×SSC, 0.1% SDS (RIP probe) or 60° C. in 0.1×SSC, 0.1% SDS (28S probe), and exposed to film with intensifying screens.

RIP Antisera and Immunoprecipitations

Rabbit polyclonal antisera recognizing RIP were prepared by Pocono Rabbit Farm & Laboratory, Inc. (Canadensis, PA) using a fusion protein containing the C-terminal 250 amino acids of mouse RIP fused to maltose-binding protein (MBP; New England Biolabs). MBP-RIP was purified by amylose chromatography and acrylamide gel elution. For immunoprecipitations, RIP was first transcribed in vitro using 15 µg full-length RIP template in a 300 µl reaction containing 3.3 mM each ATP, GTP, CTP, and UTP, 280 units RNAse inhibitor, 400 units Sp6 RNA polymerase and 1×Sp6 buffer (Boehringer Mannheim Biochemicals) at 37° C. for 2 h. Translations were carried out using a reticulocyte lysate kit containing a luciferase positive control (Oromega) using approximately 4 µCi $^{35}$S-Met per reaction. Reaction products were diluted to 1 ml in a modified RIPA buffer (0.5% NP40, 0.5% sodium deoxycholate, 0.025% SDS, 50 mM Tris, 30 mM sodium pyrophosphate, 50 mM NaF, 100 uM sodium orthovanadate [pH7.6]) containing protease inhibitors and precleared with 50 µl normal rabbit serum and 100 µl protein A sepharose (1:1). Reactions were split in half, 5 µl preimmune or immune serum was added to each, and samples were allowed to rotate for 1 h at 4° C. Complexes were precipitated with 40 µl protein A sepharose (1:1), washed 3 times with modified RIPA buffer, and resolved by SDS-PAGE.

For immunoprecipitation from metabolically labeled cells, a 150 mm plate of subconfluent NIH3T3 cells were incubated overnight in methionine-deficient DMEM (Gibco/BRL, catalog #11970-019) supplemented with $^{35}$S-methionine (~100 µCi/ml), 5% dialyzed fetal calf serum, 2 mM glutamine, penicillin (50 U/ml), and streptomycin (50 µg/ml). Cells were lysed for 15 min on ice in lysis buffer (250 mM NaCl, 50 mM HEPES-KOH, [pH 7.5], 5 mM EDTA, 0.1 mM sodium orthovanadate, 50 mM NaF, 0.1% Triton-X, 100 µg/ml PMSF, 2 µg/ml pepstatin, and 10 µg/ml each aprotonin and leupeptin), scraped, and spun at 15,000×g for 10 min. Cleared lysate was precleared once with normal rabbit serum and twice with protein A-sepharose (Pharmacia) before addition of antibodies (3 µl of preimmune or immune rabbit serum). Immune complexes were harvested with protein A-sepharose, and beads were washed four times with lysis buffer before resuspension in denaturing sample buffer. Following SDS-PAGE, the gel was enhanced for fluorography with Enlightening solution (DuPont), and dried down on absorbent paper.

Transfections and Immunofluorescence

BHK cells were plated the night before transfection at a density of 10$^4$ cells per 18 mm round coverslip (VWR Scientific). CaPO$_4$ precipitates were made by standard techniques and 18–20 h after transfection, cells were analyzed by immunofluorescence, as described by Heald et al. (Cell 74:463, 1993). Cells were fixed for 10 minutes at 3% formaldehyde and washed extensively in PBS containing 0.1% NP40. Cells were reacted with primary and secondary antibodies for 30 minutes each. Nuclei were stained with Hoechst 33258 (1 µg/ml) and mounted on slides with 90% glycerol, 0.2M Tris (pH 8.0). The 9E10 anti-myc antibody (Evan et al., 1985) was obtained as an ascites from the Harvard Cell Culture facility and used at 20 µg/ml. RIP and β-galactosidase antisera were used at dilutions of 1:200. FITC anti-mouse and Texas Red anti-rabbit secondary antibodies were obtained from Jackson Immunoresearch. Cells were examined with a Zeiss Axiophot™ fluorescent microscope.

β-Galactosidase activity in cells was visualized by fixing cells with 0.5% glutareldehyde for 15 min. followed by extensive washing in PBS containing 5 mM MgCl$_2$. Cells were stained in PBS containing 20 mM each K$_3$Fe(CN)$_6$ and K$_4$Fe(CN)$_6$·3H$_2$O, 1 mM MgCl$_2$, and 1 mg/ml X-gal (5-Bromo-4-chloro-3-indolyl-β-D-galactoside) until a suitable color developed, usually for 2–3 hours. To enumerate the fraction of blue cells which had undergone apoptotic changes, cells were transfected with one of the four plasmid combinations described and fixed 16 h after transfection.

Blue cells were included for analysis only if their morphological status could be scored unambiguously.

Other embodiments of the invention are within the following claims.

We claim:

1. An isolated DNA molecule fragment comprising a nucleotide sequence encoding a receptor interacting protein (RIP) whose amino acid sequence is selected from the group consisting of (SEQ ID NO:15) and amino acids 1–671 of (SEQ ID NO:17).

2. The isolated DNA molecule of claim 1, wherein said nucleotide sequence consists of nucleotides 1–2013 of (SEQ ID NO:16).

3. The isolated DNA molecule of claim 1, wherein said nucleotide sequence consists of nucleotides 52–2019 of (SEQ ID NO:14).

4. An isolated DNA molecule comprising a nucleotide sequence encoding an RIP death domain said death domain having an amino acid sequence selected from the group consisting of amino acids 559–656 of (SEQ ID NO:15) and amino acids 574–671 of (SEQ ID NO:17).

5. An isolated DNA molecule comprising a nucleotide sequence encoding an RIP kinase domain said kinase domain having an amino acid sequence selected from the group consisting of amino acids 2–300 of (SEQ ID NO:15) and amino acids 2–300 of (SEQ ID NO:17).

6. A transformed host cell comprising a DNA molecule according to any one of claims 1–5.

7. The transformed host cell of claim 6, said transformed host cell being a cultured cell of a metazoan animal.

8. The transformed host cell of claim 6, said transformed host cell being prokaryotic.

9. A DNA vector comprising the DNA fragment of claim 1.

* * * * *

UNITED STATES PATENT AND TRADEMARK OFFICE
CERTIFICATE OF CORRECTION

PATENT NO. : 5,674,734
DATED : October 7, 1997
INVENTORS : Philip Leder, Brian Seed, Ben Z. Stanger
Tae-Ho Lee, and Emily Kim It is certified that error appears in the above-identified patent and that said Letters Patent is hereby corrected as shown below:

Col. 37, claim 1, line 62, after "DNA", delete --molecule--.

Signed and Sealed this

Twenty-fourth Day of March, 1998

Attest:

BRUCE LEHMAN

Attesting Officer

Commissioner of Patents and Trademarks